(12) United States Patent
Wang

(10) Patent No.: US 12,023,155 B2
(45) Date of Patent: *Jul. 2, 2024

(54) POLYCARBONATE UREA/URETHANE POLYMERS FOR USE WITH ANALYTE SENSORS

(71) Applicant: Medtronic MiniMed, Inc., Northridge, CA (US)

(72) Inventor: Jenn-Hann Larry Wang, Northridge, CA (US)

(73) Assignee: MEDTRONIC MINIMED, INC., Northridge, CA (US)

(*) Notice: Subject to any disclaimer, the term of this patent is extended or adjusted under 35 U.S.C. 154(b) by 133 days.

This patent is subject to a terminal disclaimer.

(21) Appl. No.: 17/496,527

(22) Filed: Oct. 7, 2021

(65) Prior Publication Data
US 2022/0022786 A1 Jan. 27, 2022

Related U.S. Application Data

(62) Division of application No. 15/612,759, filed on Jun. 2, 2017, now Pat. No. 11,179,078.
(Continued)

(51) Int. Cl.
*A61B 5/1486* (2006.01)
*A61B 5/00* (2006.01)
(Continued)

(52) U.S. Cl.
CPC ...... *A61B 5/14865* (2013.01); *A61B 5/14532* (2013.01); *A61B 5/686* (2013.01);
(Continued)

(58) Field of Classification Search
CPC . A61B 5/14865; A61B 5/14532; A61B 5/686; A61B 5/14542; A61B 2505/07;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

WO 2017214173 12/2017

OTHER PUBLICATIONS

Xie, Xingyi, et al. "Fluorocarbon chain end-capped poly (carbonate urethane)s as biomaterials: Blood compatibility and chemical stability assessments." Journal of Biomedical Materials Research Part B: 89.1 (2009): 223-241 (Year: 2009).*
(Continued)

*Primary Examiner* — Andrey Shostak
(74) *Attorney, Agent, or Firm* — GATES & COOPER LLP

(57) ABSTRACT

Embodiments of the invention provide compositions useful in analyte sensors as well as methods for making and using such compositions and sensors. In typical embodiments of the invention, the sensor is a glucose sensor comprising an analyte modulating membrane formed from a polymer composition having carbonate and aromatic isocyanate chains, a composition observed to provide such membranes with improved material properties such as enhanced thermal and hydrolytic stability.

10 Claims, 23 Drawing Sheets

Related U.S. Application Data

(60) Provisional application No. 62/346,301, filed on Jun. 6, 2016.

(51) Int. Cl.
| | |
|---|---|
| *A61B 5/145* | (2006.01) |
| *C08G 18/40* | (2006.01) |
| *C08G 18/44* | (2006.01) |
| *C08G 18/50* | (2006.01) |
| *C08G 18/61* | (2006.01) |
| *C08G 18/72* | (2006.01) |
| *C08G 18/73* | (2006.01) |
| *C08G 18/75* | (2006.01) |
| *C08G 18/76* | (2006.01) |
| *C12Q 1/00* | (2006.01) |

(52) U.S. Cl.
CPC ......... *C08G 18/4018* (2013.01); *C08G 18/44* (2013.01); *C08G 18/5024* (2013.01); *C08G 18/61* (2013.01); *C08G 18/724* (2013.01); *C08G 18/73* (2013.01); *C08G 18/758* (2013.01); *C08G 18/7671* (2013.01); *C12Q 1/006* (2013.01); *A61B 5/14542* (2013.01); *A61B 2505/07* (2013.01); *A61B 2562/0285* (2013.01); *A61B 2562/125* (2013.01)

(58) Field of Classification Search
CPC ...... A61B 2562/0285; A61B 2562/125; C08G 18/4018; C08G 18/44; C08G 18/5024; C08G 18/61; C08G 18/724; C08G 18/73; C08G 18/758; C08G 18/7671; C12Q 1/006
See application file for complete search history.

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,642,015 | B2 | 11/2003 | Vachon et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2006/0183871 | A1 | 8/2006 | Ward et al. |
| 2007/0123819 | A1 | 5/2007 | Mernoe et al. |
| 2009/0104347 | A1 | 4/2009 | Benthem et al. |
| 2010/0160861 | A1 | 6/2010 | Causey, III et al. |
| 2012/0059117 | A1 | 3/2012 | Codina et al. |
| 2013/0178726 | A1* | 7/2013 | Wang ............... C08G 77/458 424/9.1 |
| 2015/0144486 | A1* | 5/2015 | Cho ............... G01N 27/3277 525/453 |
| 2015/0282934 | A1 | 10/2015 | Gray, Jr. et al. |

OTHER PUBLICATIONS

PCT International Search Report & Written Opinion dated Sep. 14, 2017, International Application No. PCT/US2017/036186.

Xie, Xingyi, et al. "Fluorocarbon chain end-capped poly (carbonate urethane)s as biomaterials: Blood compatibility and chemical stability assessments." Journal of Biomedical Materials Research Part B: Applied Biomaterials: An Official Journal of The Society for Biomaterials, The Japanese Society for Biomaterials, and The Australian Society for Biomaterials and the Korean Society for Biomaterials 89.1 (2009): 223-241. (Year: 2009).

PCT International Search Report & Written Opinion dated Sep. 6, 2019, International Application No. PCT/US2019/032660.

Huntsman: "The JEFFAMINE Polyetheramines". Jan. 1, 2007 (Jan. 1, 2007), XP055449578, Retrieved from the Internet: URL:http://www.huntsman.com/portal/ page/portal/performance_products/Media%20Library/global/files/jeffamine_polyetheramines.pdf [retrieved on Feb. 8, 2018] , 6 Pages.

EPO Communication dated Sep. 17, 2019 for EP Application No. 17737932.8.

(56) References Cited

OTHER PUBLICATIONS

European Examination Report dated Jan. 19, 2023 for European Patent Application No. 17737932.8.

* cited by examiner (1) PDMS (2) Jeffamine (3) 4,4'-Methylenebis(cyclohexyl isocyanate) or HMDI

OCN—HMDI—NCO (4) 4,4'-Methylenebis(phenyl isocyanate) or MDI

OCN—MDI—NCO (5) Polycarbonate diols $$HO-(R-O-\overset{\overset{O}{\|}}{C}-O)_n-R-OH$$

HO—Carbonate—OH

- Carbonic, dimethyl ester polymer with 1,6-hexanediol or 1,5-pentanediol (CAS# 126773-01-1)
- Carbonic, dimethyl ester polymer with 1,6-hexanediol (CAS# 101325-00-2)
- Mw = 1000 or 2000

FIG. 2C

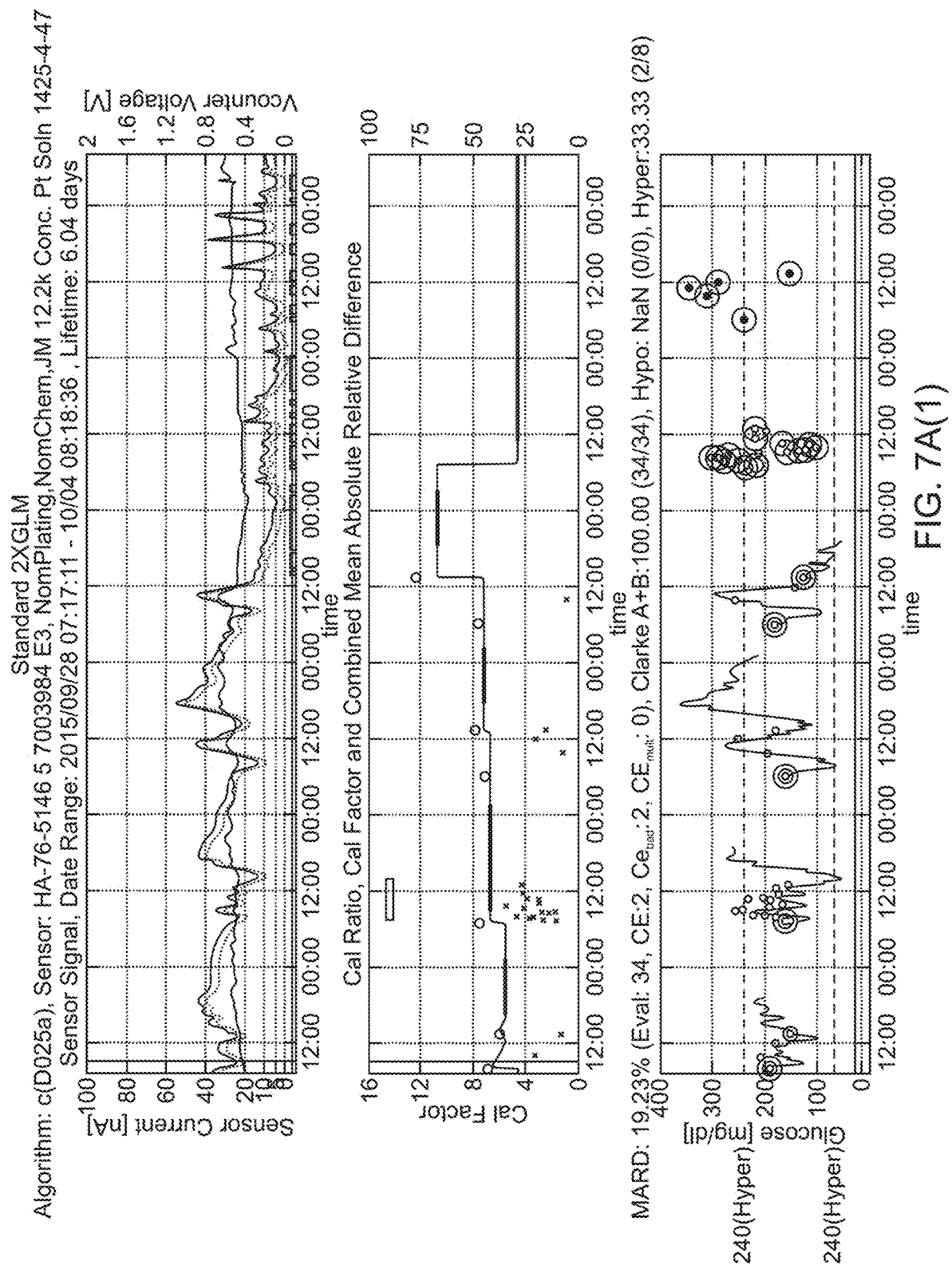
FIG. 7A(1)

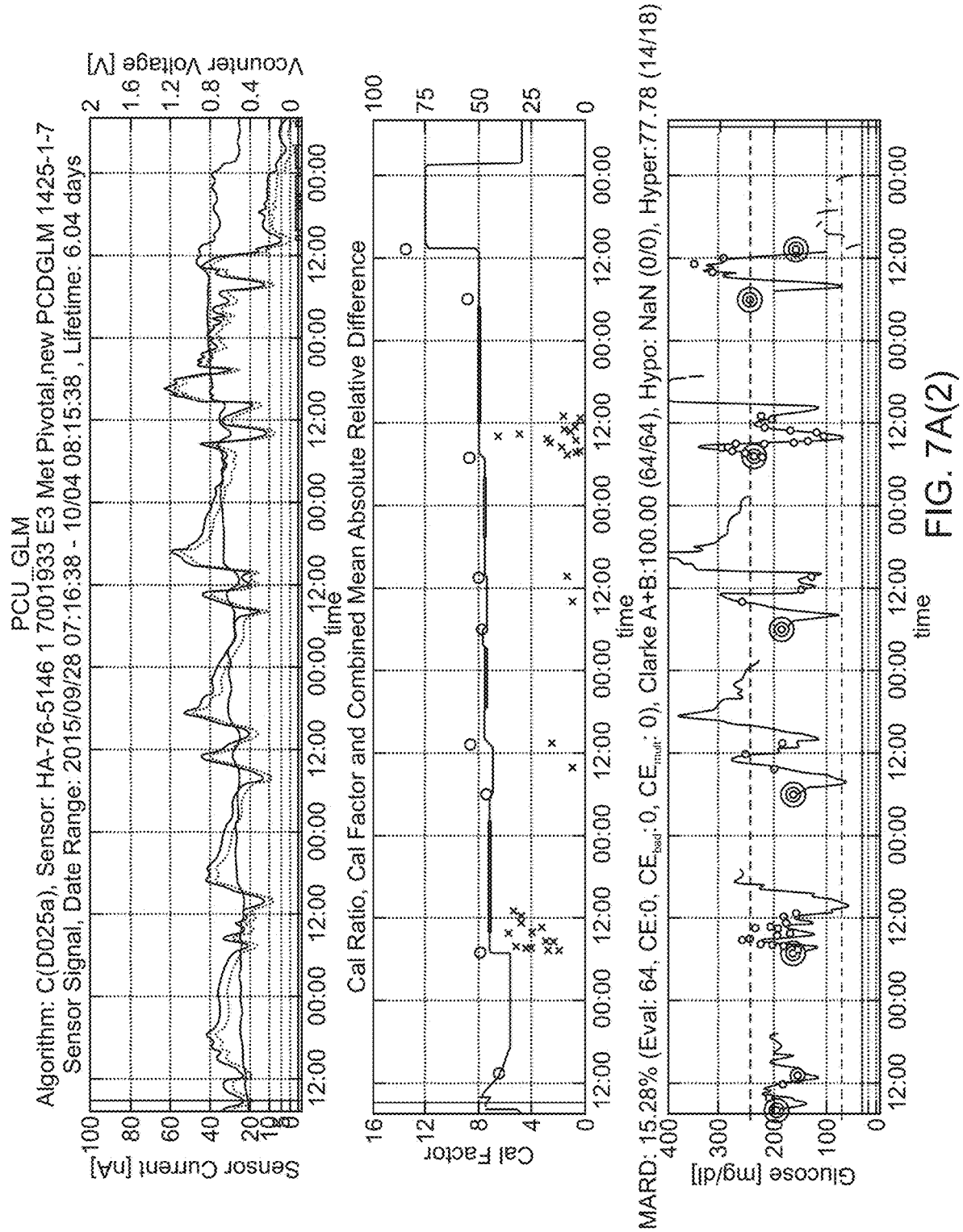
FIG. 7A(2)

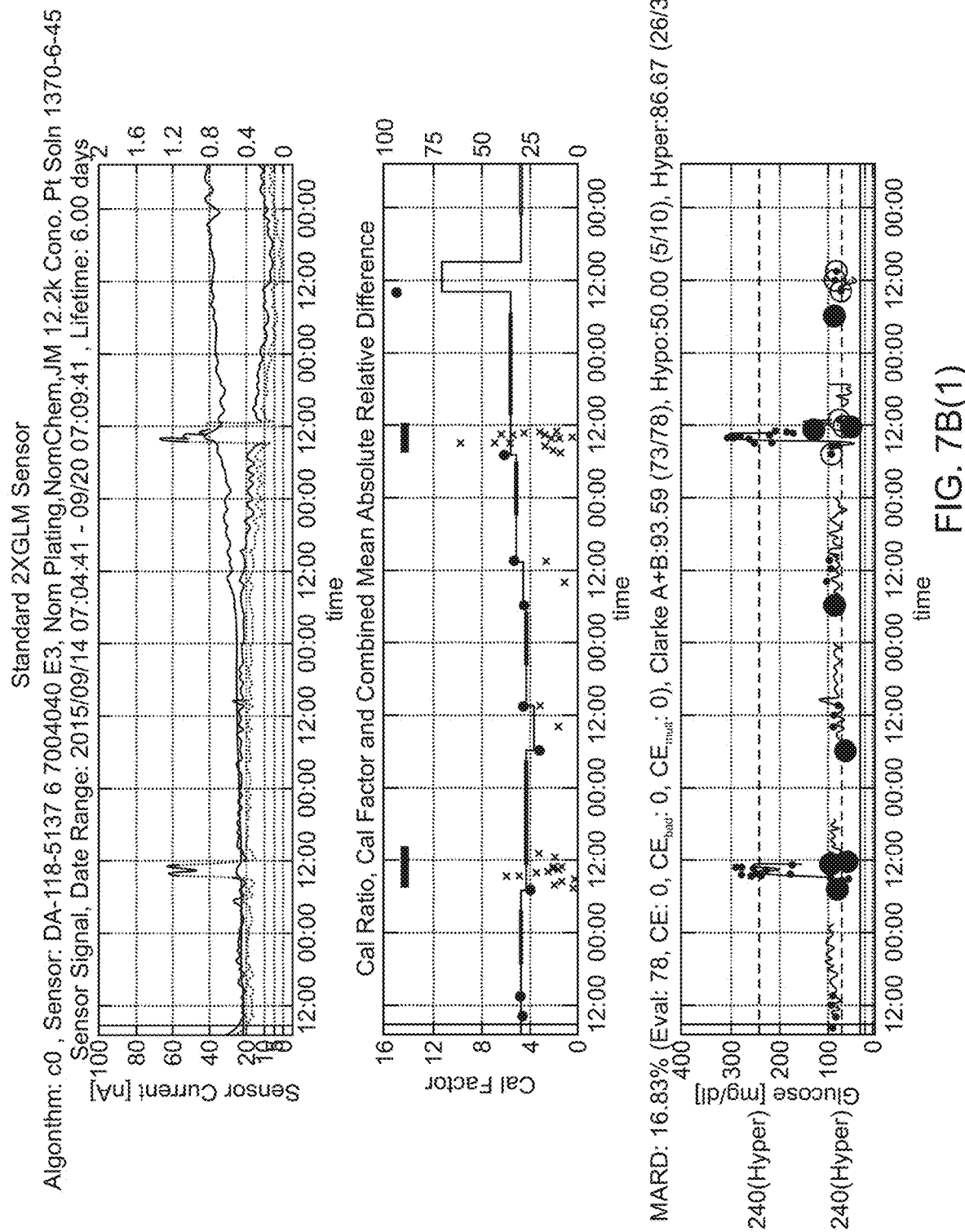
FIG. 7B(1)

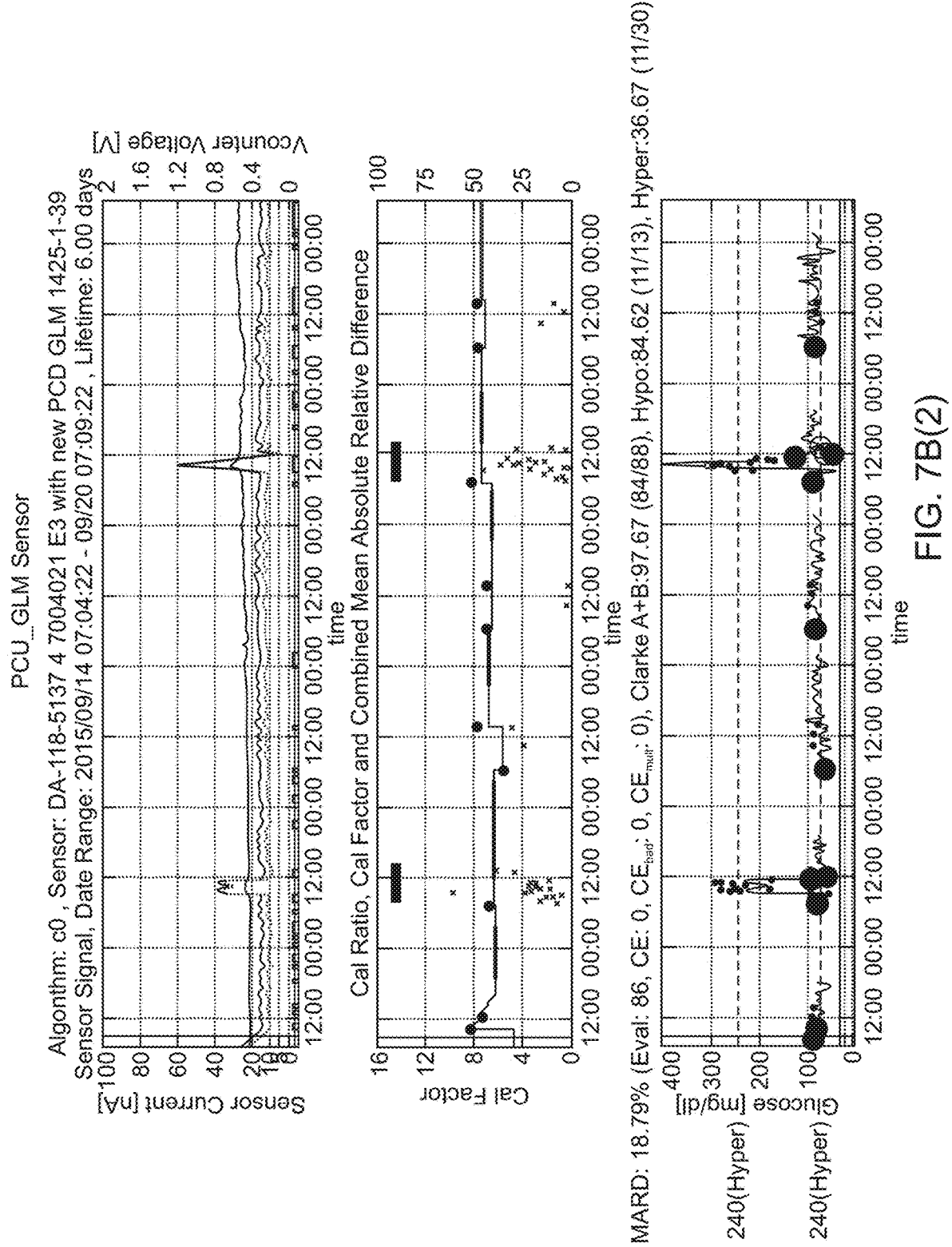
FIG. 7B(2)

Thermal Degradation Study

| Sample | Lot # | Initial Mw (kD) | Mw after aging in 100% RH and 60 °C (kD) | | Total % Loss |
|---|---|---|---|---|---|
| | | | Day 3 | Day 6 | |
| GLM #1 | 18116-42 | 223 | 77 | 52* | -77% |
| GLM #2 | 17183-100 | 198 | 111 | 66 | -67% |
| PCU_GLM#1 | 18116-5 | 187 | n/a | 100 | -46% |
| PCU_GLM#2 | 18116-39 | 205 | 124 | 102** | -50% |
| PCU_GLM#3 | 18116-58 | 200 | 163 | 145 | -28% |
| PCU_GLM#4 | 18116-60 | 199 | 174 | 161 | -19% |

Notes: *5 days
** 7 days

FIG. 8A

Formulation <Example #1>

| Batch # | Jeffamin600 | PDMS | HMDI | MDI | UH100* |
|---|---|---|---|---|---|
| 18116-5 | 32% | 32% | 23% | 0% | 13% |
| 18116-39 | 34% | 37% | 19% | 2% | 8% |
| 18116-84 | 40% | 28% | 21% | 3% | 8% |
| 18116-87 | 45% | 22% | 22% | 3% | 8% |
| 18116-94 | 45% | 22% | 12% | 8% | 8% |
| 17880-89 | 28% | 32% | 18% | 4% | 19% |
| 17880-97 | 28% | 32% | | | 19% |

\* UH100: Carbonic, dimethyl ester polymer with 1,6-hexanediol (CAS# 101325-00-2) Mw=1,000 (from UBE)

FIG. 8B

Formulation <Example #2>

| Batch # | Jeffamin900 | PDMS | HMDI | MDI | UH100 |
|---|---|---|---|---|---|
| 18116-54 | 29% | 45% | 16% | 2% | 8% |
| 18116-56 | 29% | 45% | 15% | 3% | 8% |
| 18116-57 | 29% | 46% | 14% | 3% | 8% |
| 18116-58 | 21% | 45% | 14% | 3% | 17% |
| 18116-66 | 18% | 48% | 14% | 3% | 17%* |

- PH100: Carbonic, dimethyl ester polymer with 1,6-hexanediol or 1,5-pentanediol mixture (CAS# 126773-01-1), Mw=1,000 (from UBE)

FIG. 8C

Formulation <Example #3>

| Batch # | Jeffamin600 | PDMS | HMDI | MDI | UH100 | UH200 | PH100 | PH200 |
|---|---|---|---|---|---|---|---|---|
| 18116-39 | 34% | 37% | 19% | 2% | 8% | | | |
| 18116-44 | 34% | 37% | 19% | 2% | | 8% | | |
| 18116-45 | 34% | 37% | 19% | 2% | | | 8% | |
| 18116-46 | 34% | 37% | 19% | 2% | | | | 8% |

\* UH100: Carbonic, dimethyl ester polymer with 1,6-hexanediol (CAS# 101325-00-2)
   Mw=1,000 (from UBE)
UH200: Carbonic, dimethyl ester polymer with 1,6-hexanediol (CAS# 101325-00-2)
   Mw=2,000 (from UBE)
PH100: Carbonic, dimethyl ester polymer with 1,6-hexanediol or 1,5-pentanediol (CAS# 126773-01-1)
   Mw=1,000 (from UBE)
PH200: Carbonic, dimethyl ester polymer with 1,6-hexanediol or 1,5-pentanediol (CAS# 126773-01-1)
   Mw=2,000 (from UBE)

• Based on the in vitro sensor testing, polycarbonate GLM made from various polycarbonate raw materials (UH100, UH200, PH100 and PH200) gave the similar performance.

FIG. 8D

<Example 4> Pg was not reduced after baking for Polycarbonate_GLM

- GLM without polycarbonate diols (Batch# 18088-86):
  Formulation = 41% Jeffamine600, 37% PDMS, 22% HMDI
- GLM with polycarbonate diols (Batch# 18116-5):
  Formulation = 32% Jeffamine600, 32% PDMS, 23% HMDI, 13% polycarbonate diol

| Item | Pg (original) | Pg (after baking at 60C for 7 days) | Pg (after baking, then re-dissolved and casting) |
|---|---|---|---|
| GLM (18088-86) | 5.9x10E-9 | 4.2x10E-9 | 6.2x10E-9 |
| PCU_GLM (18116-5) | 2.1x10E-9 | 2.2x10E-9 | N/A |

*Pg = glucose permeability, unit $cm^2/sec$

FIG. 8E

Thermal/hydrolysis result summary

Study #1 (12/2013)

| Sample | Lot # | Initial MW (kD) | MW after aging in 100% RH and 60oC (kD) | | | Total % Loss |
|---|---|---|---|---|---|---|
| | | | Day 1 | Day 3 | Day 6 | |
| GLM #1 | 16601-24 | 149 | 108 | 89 | 63 | 58% |
| GLM #2 | 17183-65 | 171 | 88 | 39 | 22 | 87% |
| GLM #3 | 17183-100 | 198 | 141 | 111 | 66 | 67% |
| GLM #4 with 10% MDI | 17183-98 | 230 | 224 | 197 | 165 | 28% |
| GLM #5 with 10% MDI | 17580-5 | 176 | 173 | 167 | 131 | 26% |

Study #2 (1/2014)

| Sample | Lot # | MW (kD) | MW after aging in 100% RH and 60oC (kD) | | | | Total % Loss |
|---|---|---|---|---|---|---|---|
| | | | Day 1 | Day 2 | Day 3 | Day 6 | Day 7 | |
| GLM #6 | 16601-24 | 140 | 110 | 96 | 85 | X | 62 | 56% |
| GLM #7 | 17183-67 | 146 | 103 | 86 | 70 | X | 47 | 68% |
| GLM #8 | 17183-100 | 198 | 145 | 118 | 105 | X | 82 | 59% |
| GLM #9 with 10% MDI | 17580-17a | 144 | 126 | 114 | 104 | 95 | 87 | 40% |
| GLM #10 with 10% MDI | 17580-17b | 140 | 131 | 125 | 114 | 100 | 96 | 31% |

Study #3 (7/2015)

| Sample | Lot # | MW (kD) | MW after aging in 100% RH and 60oC (kD) | | | | Total % Loss |
|---|---|---|---|---|---|---|---|
| | | | Day 5 | Day 7 | Day 14 | Day 21 | Day 35 | |
| GLM#11 with 20%PCD & 10%MDI | 17880-97 | 239 | 217 | 209 | 148 | 131 | 99 | 59% |

FIG. 9

POLYCARBONATE UREA/URETHANE POLYMERS FOR USE WITH ANALYTE SENSORS

CROSS REFERENCE TO RELATED APPLICATIONS

This application is a divisional application which claims the benefit under 35 U.S.C. § 120 and § 121 of U.S. patent application Ser. No. 15/612,759, filed Jun. 2, 2017, which claims priority under Section 119(e) from U.S. Provisional Application Ser. No. 62/346,301, filed Jun. 6, 2016, the contents of which are incorporated herein by reference.

BACKGROUND OF THE INVENTION

1. Field of the Invention

This invention relates to biosensors such as glucose sensors used in the management of diabetes and materials for making such sensors, for example polymeric compositions useful for biosensor membranes.

2. Description of Related Art

Analyte sensors such as biosensors include devices that use biological elements to convert a chemical analyte in a matrix into a detectable signal. There are many types of biosensors used to detect wide variety of analytes. Perhaps the most studied type of biosensor is the amperometric glucose sensor, an apparatus commonly used to monitor glucose levels in individuals with diabetes.

A typical glucose sensor works according to the following chemical reactions:

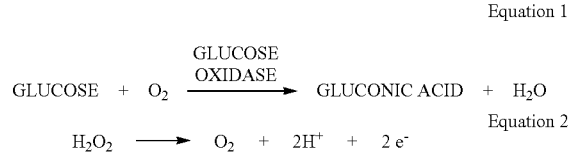

Equation 1

$$\text{GLUCOSE} + O_2 \xrightarrow{\text{GLUCOSE OXIDASE}} \text{GLUCONIC ACID} + H_2O$$

Equation 2

$$H_2O_2 \longrightarrow O_2 + 2H^+ + 2e^-$$

The glucose oxidase is used to catalyze the reaction between glucose and oxygen to yield gluconic acid and hydrogen peroxide as shown in equation 1. The $H_2O_2$ reacts electrochemically as shown in equation 2, and the current is measured by a potentiostat. The stoichiometry of the reaction provides challenges to developing in vivo sensors. In particular, for optimal sensor performance, sensor signal output should be determined only by the analyte of interest (glucose), and not by any co-substrates ($O_2$) or kinetically controlled parameters such as diffusion. If oxygen and glucose are present in equimolar concentrations, then the $H_2O_2$ is stoichiometrically related to the amount of glucose that reacts at the enzyme; and the associated current that generates the sensor signal is proportional to the amount of glucose that reacts with the enzyme. If, however, there is insufficient oxygen for all of the glucose to react with the enzyme, then the current will be proportional to the oxygen concentration, not the glucose concentration. Consequently, for the sensor to provide a signal that depends solely on the concentrations of glucose, glucose must be the limiting reagent, i. e. the $O_2$ concentration must be in excess for all potential glucose concentrations. A problem with using such glucose sensors in vivo, however, is that the oxygen concentration where the sensor is implanted in vivo is low relative to glucose, phenomena which can compromise the accuracy of sensor readings.

There are a number of approaches to solving the oxygen deficit problem. One is to use a homogenous polymer membrane with hydrophobic and hydrophilic regions that control oxygen and glucose permeability. For example, Van Antwerp et al. developed linear polyurea membranes comprising polyethylene glycol and silicone hydrophobic components that allow for a high oxygen permeability in combination with hydrophilic component that allow for a limited glucose permeability (see e.g. U.S. Pat. Nos. 5,777,060, 5,882,494 and 6,642,015). While having a number of useful and desirable characteristics, such polymeric compositions can experience some degradation over time under high temperature and high humidity conditions. In view of this, there is a need in the art for more robust polymeric membrane compositions that can, for example, be used to address the oxygen deficit problem that is observed in glucose sensors that incorporate glucose oxidase.

SUMMARY OF THE INVENTION

The invention disclosed herein provides biosensors such as amperometric glucose sensors and methods and materials for making such sensors. Embodiments of the invention include a sensor having a plurality of layered elements including an analyte limiting membrane comprising a polymeric compound designed to include carbonate and aromatic isocyanate chains in amounts observed to contribute to the thermal and hydrolytic stability of such polymers. As disclosed herein, when these polymer compositions are used to form the analyte limiting membranes in glucose sensors, the resultant sensors exhibit enhanced the long term stability profiles as compared to conventional polymer compositions that do not include such constituents.

The invention disclosed herein has a number of embodiments. A typical embodiment of the invention is an amperometric analyte sensor apparatus comprising an electrode; an analyte sensing layer disposed on the electrode and an analyte modulating layer disposed on the analyte sensing layer. In such embodiments of the invention, the analyte modulating layer comprises a polyurea-urethane copolymer formed from a reaction mixture comprising a diisocyanate, a hydrophilic polymer comprising a hydrophilic diol or hydrophilic diamine, a siloxane having an amino, hydroxyl or carboxylic acid functional group at a terminus, and a polycarbonate diol. As discussed below, these polymer compositions exhibit a combination of desirable properties including: an enhanced thermal stability as well as a permeability to molecules such as glucose that is relatively stable over time and a range of temperatures. In addition, these polymer compositions exhibit good mechanical properties for use as an outer polymeric membrane in a variety of analyte sensors (e.g. glucose sensor that are implantable in vivo). Consequently, analyte sensors that incorporate such polymeric membranes exhibit an enhanced in-vivo performance profile.

Embodiments of the invention include methods of making sensors using polymeric compositions formed to have one or more selected material properties. In one illustrative embodiment, a method of making an analyte sensor for implantation within a mammal comprises the steps of: providing a base layer; forming a conductive layer on the base layer, wherein the conductive layer includes a working electrode; forming an analyte sensing layer on the conductive layer, wherein the analyte sensing layer includes an oxidoreductase such as glucose oxidase; and then forming an analyte modulating layer on the analyte sensing layer. In such embodiments, the analyte modulating layer comprises a polyurea-urethane copolymer formed from a reaction mixture made by combining a diisocyanate; a hydrophilic polymer comprising a hydrophilic diol or hydrophilic diamine; a siloxane having an amino, hydroxyl or carboxylic acid functional group at a terminus; and a polycarbonate diol. In some embodiments of the invention, the polyurea-urethane copolymer is formed from a reaction mixture selected to exhibit a more uniform glucose permeability profile over time as compared to an equivalent analyte sensor having an analyte modulating layer formed from a reaction mixture that does not include the polycarbonate diol. In some embodiments of the invention, the polyurea-urethane copolymer is formed from a reaction mixture selected to exhibit an improved resistance to degradation/damage caused by ebeam radiation and/or ethylene oxide as compared to an equivalent analyte sensor having an analyte modulating layer formed from a reaction mixture that does not include the polycarbonate diol. In other embodiments of the invention, the polyurea-urethane copolymer is formed from a reaction mixture selected to exhibit an improved thermal stability over time as compared to an equivalent analyte sensor having an analyte modulating layer formed from a reaction mixture that does not include the polycarbonate diol. In some embodiments of the invention, the polyurea-urethane copolymer is formed from a reaction mixture selected to exhibit an improved resistance to oxidation over time as compared to an equivalent analyte sensor having an analyte modulating layer formed from a reaction mixture that does not include the polycarbonate diol. In some embodiments of the invention, the polyurea-urethane copolymer is formed from a reaction mixture selected to produce a polymeric membrane that exhibits less deformation over time as compared to an equivalent analyte sensor having an analyte modulating layer formed from a reaction mixture that does not include the polycarbonate diol.'

Embodiments of the invention include compositions composed of a biocompatible polyurea-urethane copolymer formed from a reaction mixture comprising a diisocyanate, a hydrophilic polymer comprising a hydrophilic diol or hydrophilic diamine, a siloxane having an amino, hydroxyl or carboxylic acid functional group at a terminus; and a polycarbonate diol. Typically in such compositions, the diisocyanate comprises a hexamethylene diisocyanate and/or a methylene diphenyl diisocyanate, the hydrophilic polymer comprising a hydrophilic diol or hydrophilic diamine comprises a JEFFAMINE, the siloxane having an amino, hydroxyl or carboxylic acid functional group at a terminus comprises a polydimethylsiloxane, and the polycarbonate diol comprises a (poly(1,6-hexyle carbonate) diol and/or a poly(1,6 hexyl-1,5 pentyl carbonate) diol. Optionally in such embodiments, the diisocyanate comprises: from 17% to 23% weight percent hexamethylene diisocyanate and from 0% to 8.5% weight percent methylene diphenyl diisocyanate; the JEFFAMINE comprises from 28% to 51% weight percent JEFFAMINE 600 and/or JEFFAMINE 900; the polydimethylsiloxane comprises from 14% to 32% weight percent polydimethylsiloxane-A15); and the polycarbonate diol comprises from 7.5% to 19% weight percent (poly(1,6-hexyle carbonate) diol. In illustrative working embodiments of the invention, the diisocyanate comprises about 22% hexamethylene diisocyanate and about 3.5% methylene diphenyl diisocyanate; the JEFFAMINE comprises about 45% JEFFAMINE 600 and/or JEFFAMINE 900; the polydimethylsiloxane comprises about 22.5% polydimethylsiloxane-A15); and the polycarbonate diol comprises about 7.5% (poly(1,6-hexyle carbonate) diol.

Another embodiment of the invention is a method of making a biocompatible membrane by forming a reaction mixture comprising: a diisocyanate; a hydrophilic polymer comprising a hydrophilic diol or hydrophilic diamine; a siloxane having an amino, hydroxyl or carboxylic acid functional group at a terminus; and a polycarbonate diol; and allowing these components to react together to form a polyurea-urethane copolymer. Typically in such embodiments, water is added as a chain extender after the reagents in the reaction mixture of the polyurea-urethane copolymer. In certain embodiments of the invention, the polycarbonate diol is not added all at once and is added in aliquots. In illustrative embodiments of the invention, the polycarbonate diol is added to the reaction mixture in a first aliquot; a second aliquot and a third aliquot. Optionally for example, the first aliquot comprises more than 30% of the total amount of polycarbonate diol (e.g. about 40%), the second aliquot comprises less than 30% of the total amount of polycarbonate diol (e.g. about 20%); and the third aliquot comprises more than 30% of the total amount of polycarbonate diol (e.g. about 40%). In addition, 9 in certain embodiments of the invention, a first aliquot can be combined with the other compounds in an initial reaction mixture, the second aliquot can be added at least 1, 2 or 3 hours after the first aliquot; and a third aliquot can be added at least 5, 10, 15 or 20 hours after the second aliquot.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

Referring now to the drawings in which like reference numbers represent corresponding parts throughout:

FIGS. 2A-C show the chemical structures of raw materials used in the polycarbonate urea glucose limiting membrane (GLM), in accordance with one or more embodiments of the invention. FIG. 2A shows the chemical structures of PDMS and Jeffamine. FIG. 2B shows the chemical structures of 4,4'-Methylenebis(cyclohexyl isocyanate) or HMDI and 4,4'-Methylenebis(phenyl isocyanate) or MDI. FIG. 2C shows the chemical structure of polycarbonate diols;

FIG. 10A shows bubbles (or craters) generated at the counter electrode after usage. Bubbles formation at the counter electrode may trigger delamination or unwanted biological responses (due to texture change or rough surface). FIG. 10B shows that the MDI_polycarnobate_GLM can enhance the GLM adhesion, so that bubbles (or craters) are not generated at the counter electrode after usage;

FIGS. 7A-E show various graphs illustrating dog result comparisons between standard 2×GLM and PCU_GLM, in accordance with one or more embodiments of the invention. FIG. 7A shows in vitro dog result comparisons. FIG. 7B shows in vivo dog result comparisons. FIG. 7C shows sensor data from an E3 PCU GLM formulation. FIG. 7D shows sensor data from an E3 PCD GLM formulation. FIG. 7E shows sensor data from a PCD GLM formulation;

FIGS. 8A-E show results from thermal degradation studies for various formulations and the compositions of the formulations, in accordance with one or more embodiments of the invention. FIG. 8A shows the results from a thermal degradation study. FIGS. 8B-D show the compositions of various formulations. FIG. 8E provides data showing that glucose permeability (Pg) was not reduced after baking for polycarbonate_GLM;

FIG. 9 shows a summary of the results from thermal/hydrolysis studies of various sample formulations, in accordance with one or more embodiments of the invention. The thermal degradation test results demonstrate that MDI and polycarbonates chains can help (slow down) the GLM degradation process;

DETAILED DESCRIPTION OF THE EMBODIMENTS

Figure 1:
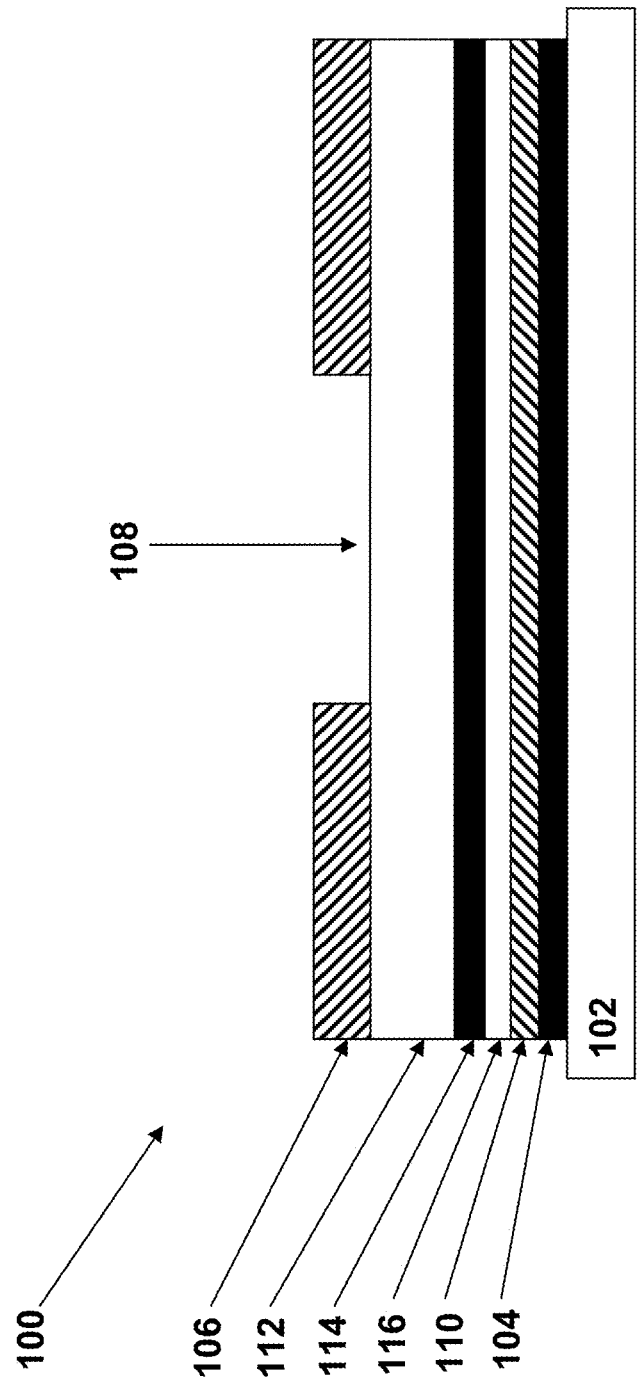
FIG. 1 provides a diagrammatic view of one embodiment of an amperometric analyte sensor having a plurality of layered materials/elements, in accordance with one or more embodiments of the invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. A number of terms are defined below. All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. "50 mol %") are understood to be modified by the term "about".

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

As discussed in detail below, embodiments of the invention relate to the use of an electrochemical sensor that exhibits a novel constellation of material and functional elements. Such sensors incorporate new polymeric compositions in order to form robust analyte modulating membranes, ones having a unique set of technically desirable material properties. The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors comprise a polymeric membrane surrounding the enzyme through which an analyte migrates prior to reacting with the enzyme. The product is then measured using electrochemical methods and thus the output of an electrode system functions as a measure of the analyte. In some embodiments, the sensor can use an amperometric, coulometric, conductimetric, and/or potentiometric technique for measuring the analyte.

Analyte modulating compositions such as those useful as glucose limiting membranes in amperometric glucose sensors include polymeric compositions formed from biocompatible polymeric polyurea materials (see, e.g., the contexts of which re incorporated by reference). Such compositions can exhibit stable glucose and oxygen permeabilities, low protein adsorption rates, and biocompatibility. However, due to the content of PEG chains, it suffered some degradation issue under high temperature and/or high humidity conditions. As disclosed in detail below, we have discovered that certain carbonate and aromatic isocyanate compounds can be added to a polymerization reaction so as to replace some portions of PDMS and HMDI polymeric chain elements. Both compounds have been discovered to increase the thermal and hydrolysis resistance of these polymers under high temperature and high humidity conditions. In addition, their chemical structures provide evidence that such compositions have a very good e-beam resistance. The carbonate materials useful in embodiments of the invention include, but are not limited to, polycarbonate diols (e.g. butanediol or hexanediol or similar compounds). In the illustrative embodiments of the invention, their Mw is from 500 to 2000 Daltons. The aromatic isocyanate materials useful in embodiments of the invention include, but not limited to, MDI or similar compounds.

The addition of MDI can improve the thermal and e-beam resistance of polymeric compositions used as analyte modulating (e.g. glucose limiting) compositions through its benzene ring structure. The benzene ring also serves as a good free-radical scavenger to prevent oxidation of polymeric constituents. The polycarbonate diol can provide better thermal and hydrolysis resistances through its carbonate structure (vs. ether or ester chains). The addition of polycarbonate segment in the polymer backbone can prevent the unwanted deformation of a layer of a polymer composition that is disposed on an electrode of an amperometric glucose sensor. Both gas and water are generated on a counter electrode between analyte sensing layers (e.g. ones comprised of an enzyme such as GOX) and analyte modulating (e.g. Glucose Limiting Membrane) layers, which can cause sensor failure (signal drifting) after a long usage. In this context, the polycarbonate segments in the GLM backbone can prevent/reduce the chain rotation of PDMS in the GLM film, so the glucose permeability (Pg) of GLM will not be gradually reduced over time due to the hydrophilic chains (Jeffamine or PEG) was wrapped/entrapped by the hydrophobic PDMS chains, especially for the low Pg GLM cases. In certain embodiments, in order to make a homogeneous urethane/urea copolymer, the synthesis will involve 3 raw material injections after different timings. The raw materials were injected at 4-2-4 ratio at time=0, 4, 24 hours, respectively. The addition of polycarbonate chains in the GLM can prevent the Pg change/reduction due to the PDMS chain rotation/tangling over time, especially for low Pg GLM films. In order to reduce thermal/radiation/oxidation degradation, the desired MDI content in the final polymer can be from 2% to 25%. In order to prevent the film deformation or Pg reduction due to silicone chain rotation over time, the desired polycarbonate content in the final polymer can be from 8% to 30%. Polycarbonate GLM showed good adhesion with AP, no more craters (bubbles) formed after testing Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,939 5,605,152, 4,431,004, 4,703,756, 6,514,718, 5,985,129, 5,390,691, 5,391, 250, 5,482,473, 5,299,571, 5,568,806, 5,494,562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. analyte modulating membranes made from polycarbonate polymeric compositions) can be adapted for use with any one of the wide variety of sensors known in the art. The analyte sensor elements, architectures and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Specific aspects of embodiments of the invention are discussed in detail in the following sections.
Typical Elements, Configurations and Analyte Sensors of the Invention
Optimized Sensor Elements of the Invention A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16: 1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology. One problem associated with the use of certain amperometric transducers, however, include a suboptimal reaction stoichiometry. As discussed in detail below, these problems are addressed by using the polycarbonate polymeric membrane(s) disclosed herein, membranes which can modulate the transport properties of different compounds whose reaction creates a signal at the hydrogen peroxide-based amperometric transducing element. Consequently, these membranes can be used for example with a variety of $H_2O_2$ based analyte sensors that benefit from optimized reaction stoichiometries.

As noted above, embodiments of the invention include sensor membranes made from polycarbonate polymer compositions. As is known in the art, a polymer comprises a long or larger molecule consisting of a chain or network of many repeating units, formed by chemically bonding together many identical or similar small molecules called monomers. A copolymer or heteropolymer is a polymer derived from two (or more) monomeric species, as opposed to a homopolymer where only one monomer is used. Copolymers may also be described in terms of the existence of or arrangement of branches in the polymer structure. Linear copolymers consist of a single main chain whereas branched copolymers consist of a single main chain with one or more polymeric side chains. Sensor membranes made from polycarbonate polymeric compositions disclosed herein can optimize analyte sensor function including sensor sensitivity, stability and hydration profiles. In addition, by optimizing the stoichiometry of reactant species over a range of sensor temperatures, the membranes disclosed herein can optimize the chemical reactions that produce the critical measurable signals that correlate with the levels of an analyte of interest (e.g. glucose). The following sections describe illustrative sensor elements, sensor configurations and methodological embodiments of the invention.

Certain amperometric sensor design used with embodiments of the invention comprise a plurality of layered elements including for example a base layer having an electrode, an analyte sensing layer (e.g. one comprising glucose oxidase) and an analyte modulating layer that functions in analyte diffusion control (e.g. to modulate the amounts of glucose and oxygen exposed to the analyte sensing layer). One such sensor embodiment is shown in FIG. 1. Layered sensor designs that incorporate the polycarbonate polymeric compositions disclosed herein as the analyte modulating layer exhibit a constellation of material properties that overcome challenges observed in a variety of sensors including electrochemical glucose sensors that are implanted in vivo. For example, sensors designed to measure analytes in aqueous environments (e.g. those implanted in tian) typically require wetting of the layers prior to and during the measurement of accurate analyte reading. Because the properties of a material can influence the rate at which it hydrates, the material properties of membranes used in aqueous environments ideally will facilitate sensor wetting to, for example, minimize the time period between the sensor's introduction into an aqueous environment and its ability to provide accurate signals that correspond to the concentrations of an analyte in that environment. Embodiments of the invention that comprise polycarbonate polymeric compositions address such issues by facilitating sensor hydration.

Moreover, with electrochemical glucose sensors that utilize the chemical reaction between glucose and glucose oxidase to generate a measurable signal, the material of the analyte modulating layer should not exacerbate (and ideally should diminish) what is known in the art as the "oxygen deficit problem". Specifically, because glucose oxidase based sensors require both oxygen ($O_2$) as well as glucose to generate a signal, the presence of an excess of oxygen relative to glucose, is necessary for the operation of a glucose oxidase based glucose sensor. However, because the concentration of oxygen in subcutaneous tissue is much less than that of glucose, oxygen can be the limiting reactant in the reaction between glucose, oxygen, and glucose oxidase in a sensor, a situation which compromises the sensor's ability to produce a signal that is strictly dependent on the concentration of glucose. In this context, because the properties of a material can influence the rate at which compounds diffuse through that material to the site of a measurable chemical reaction, the material properties of an analyte modulating layer used in electrochemical glucose sensors that utilize the chemical reaction between glucose and glucose oxidase to generate a measurable signal, should not for example, favor the diffusion of glucose over oxygen in a manner that contributes to the oxygen deficit problem. Embodiments of the invention that comprise the polycarbonate polymeric compositions disclosed herein do not contribute to, and instead function to ameliorate, the oxygen deficit problem.

In addition, sensor designs that use the polycarbonate polymeric compositions disclosed herein as a analyte modulating layer can also overcome complications observed with the use of sensor materials that can exhibit different diffusion profiles (e.g. a rate at which an analyte diffuses therethrough) at different temperatures. In particular, for optimized sensor performance, sensor signal output over a range of temperatures should be determined only by the levels of analyte of interest (e.g. glucose), and not by any co-substrates (e.g. $O_2$) or kinetically controlled parameters (e.g. diffusion). As is known in the art however, the diffusion of compounds through a polymeric matrix can be temperature dependent. In situations where an analyte (e.g. glucose) diffuses through a polymer to react a site where it reacts with another compound (e.g. glucose oxidase), such temperature dependent diffusion profiles can influence the stoichiometry of the reaction relied upon to generate the sensor signal, thereby confounding artisans' efforts to make sensor signal output depend only on the concentration of an analyte of interest over a range of temperatures. Analyte modulating compositions made from materials having an analyte (e.g. glucose) diffusion profile that is stable over a range of temperatures (e.g. from 22 to 40 degrees centigrade) consequently address such issues.

The invention disclosed herein provides polycarbonate polymeric compositions useful for example as membranes for biosensors such as amperometric glucose sensors. Embodiments of the invention include for example a sensor having a plurality of layered elements including an analyte limiting membrane comprising a polycarbonate polymeric composition. Such polymeric membranes are particularly useful in the construction of electrochemical sensors for in vivo use. The membrane embodiments of the invention allow for a combination of desirable properties including: an enhanced hydration profile as well as a permeability to molecules such as glucose that is stable over a range of temperatures. In addition, these polymeric membranes exhibit good mechanical properties for use as an outer polymeric membrane. Consequently, glucose sensors that incorporate such polymeric membranes show a highly desirable in-vivo performance profile.

Embodiments of the invention include both materials (e.g. polycarbonate polymeric compositions) as well as architectures that designed to facilitate sensor performance. For example, in certain embodiments of the invention, the conductive layer comprises a plurality of working electrodes and/or counter electrodes and/or reference electrodes (e.g. 3 working electrodes, a reference electrode and a counter electrode), in order to, for example, avoid problems associated with poor sensor hydration and/or provide redundant sensing capabilities. Optionally, the plurality of working, counter and reference electrodes are configured together as a unit and positionally distributed on the conductive layer in a repeating pattern of units. In certain embodiments of the invention, the base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment. Typically, the sensor is operatively coupled to a sensor input capable of receiving a signal from the sensor that is based on a sensed analyte; and a processor coupled to the sensor input, wherein the processor is capable of characterizing one or more signals received from the sensor. In some embodiments of the invention, a pulsed voltage is used to obtain a signal from one or more electrodes of a sensor.

The sensors disclosed herein can be made from a wide variety of materials known in the art. In one illustrative embodiment of the invention, the analyte modulating layer comprises a polyurethane/polyurea polymer formed from a mixture comprising: a diisocyanate; a hydrophilic polymer comprising a hydrophilic diol or hydrophilic diamine; and a siloxane having an amino, hydroxyl or carboxylic acid functional group at a terminus; with this polymer then polycarbonate with a branched acrylate polymer formed from a mixture comprising: a butyl, propyl, ethyl or methyl-acrylate; an amino-acrylate; a siloxane-acrylate; and a poly(ethylene oxide)-acrylate. Optionally, additional materials can be included in these polymeric blends. For example, certain embodiments of the branched acrylate polymer are formed from a reaction mixture that includes a hydroxyl-acrylate compound (e.g. 2-hydroxyethyl methacrylate).

As used herein, the term "polyurethane/polyurea polymer" refers to a polymer containing urethane linkages, urea linkages or combinations thereof. As is known in the art, polyurethane is a polymer consisting of a chain of organic units joined by urethane (carbamate) links. Polyurethane polymers are typically formed through step-growth polymerization by reacting a monomer containing at least two isocyanate functional groups with another monomer containing at least two hydroxyl (alcohol) groups in the presence of a catalyst. Polyurea polymers are derived from the reaction product of an isocyanate component and a diamine. Typically, such polymers are formed by combining diisocyanates with alcohols and/or amines. For example, combining isophorone diisocyanate with PEG 600 and aminopropyl polysiloxane under polymerizing conditions provides a polyurethane/polyurea composition having both urethane (carbamate) linkages and urea linkages. Such polymers are well known in the art and described for example in U.S. Pat. Nos. 5,777,060, 5,882,494 and 6,632,015, and PCT publications WO 96/30431; WO 96/18115; WO 98/13685; and WO 98/17995, the contents of each of which is incorporated by reference.

The polyurethane/polyurea compositions of the invention are prepared from biologically acceptable polymers whose hydrophobic/hydrophilic balance can be varied over a wide range to control the ratio of the diffusion coefficient of oxygen to that of glucose, and to match this ratio to the design requirements of electrochemical glucose sensors intended for in vivo use. Such compositions can be prepared by conventional methods by the polymerization of monomers and polymers noted above. The resulting polymers are soluble in solvents such as acetone or ethanol and may be formed as a membrane from solution by dip, spray or spin coating.

Diisocyanates useful in this embodiment of the invention are those which are typically those which are used in the preparation of biocompatible polyurethanes. Such diisocyanates are described in detail in Szycher, SEMINAR ON ADVANCES IN MEDICAL GRADE POLYURETHANES, Technomic Publishing, (1995) and include both aromatic and aliphatic diisocyanates. Examples of suitable aromatic diisocyanates include toluene diisocyanate, 4,4'-diphenylmethane diisocyanate, 3,3'-dimethyl-4,4'-biphenyl diisocyanate, naphthalene diisocyanate and paraphenylene diisocyanate. Suitable aliphatic diisocyanates include, for example, 1,6hexamethylene diisocyanate (HDI), trimethylhexamethylene diisocyanate (TMDI), trans1,4-cyclohexane diisocyanate (CHDI), 1,4-cyclohexane bis(methylene isocyanate) (BDI), 1,3-cyclohexane bis(methylene isocyanate) ($H_6$XDI), isophorone diisocyanate (IPDI) and 4,4'-methylenebis(cyclohexyl isocyanate) ($H_2$MDI). In some embodiments, the diisocyanate is isophorone diisocyanate, 1,6-hexamethylene diisocyanate, or 4,4'methylenebis(cyclohexyl isocyanate). A number of these diisocyanates are available from commercial sources such as Aldrich Chemical Company (Milwaukee, Wis., USA) or can be readily prepared by standard synthetic methods using literature procedures.

The quantity of diisocyanate used in the reaction mixture for the polyurethane/polyurea polymer compositions is typically about 50 mol % relative to the combination of the remaining reactants. More particularly, the quantity of diisocyanate employed in the preparation of the polyurethane/polyurea polymer will be sufficient to provide at least about 100% of the —NCO groups necessary to react with the hydroxyl or amino groups of the remaining reactants. For example, a polymer which is prepared using x moles of diisocyanate, will use a moles of a hydrophilic polymer (diol, diamine or combination), b moles of a silicone polymer having functionalized termini, and c moles of a chain extender, such that x=a+b+c, with the understanding that c can be zero.

Figure 4A:
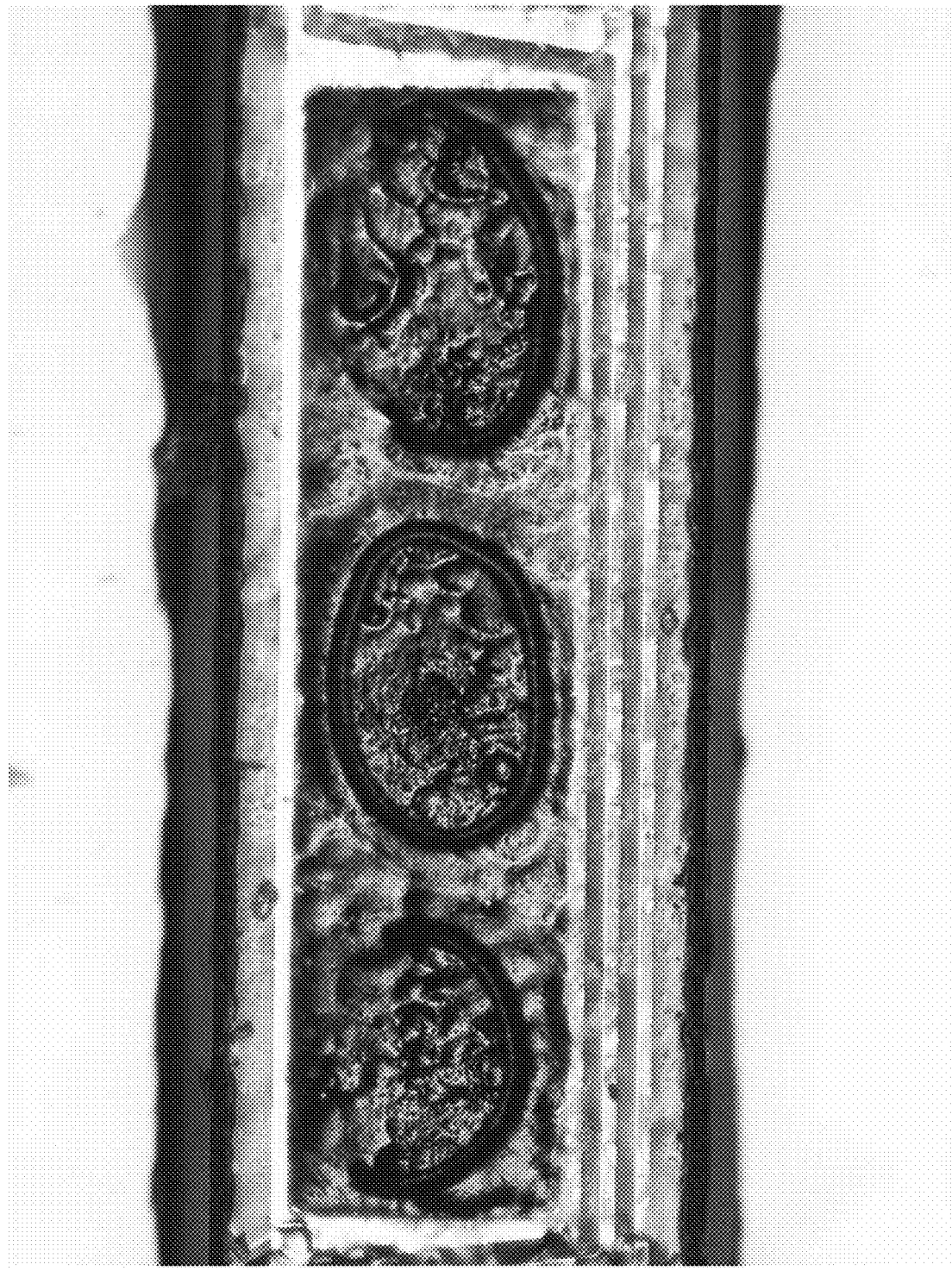
FIGS. 4A-B show a comparison of morphology of various counter and working electrodes after testing, in accordance with one or more embodiments of the invention.
Figure 4B:
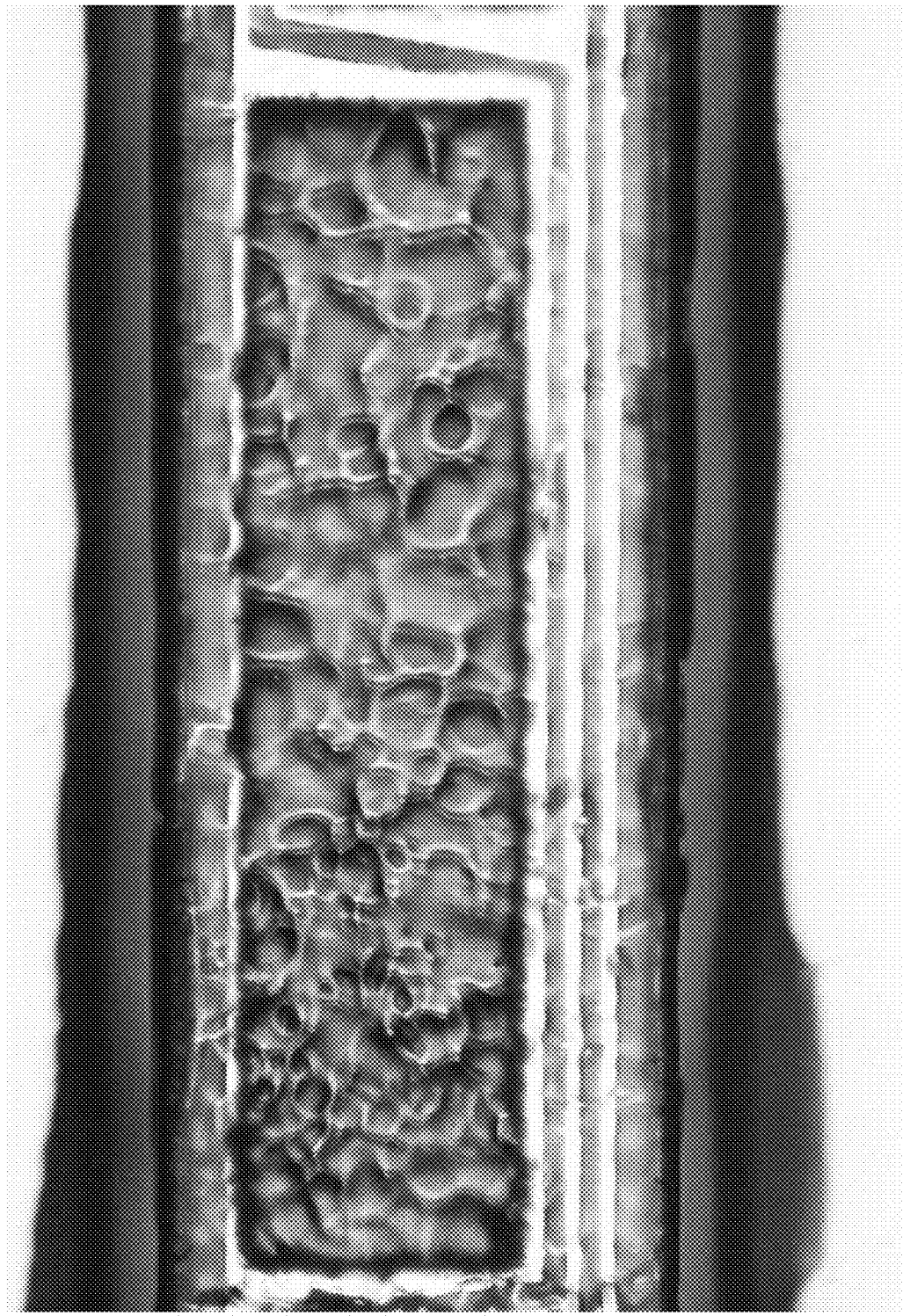
Figure 5:
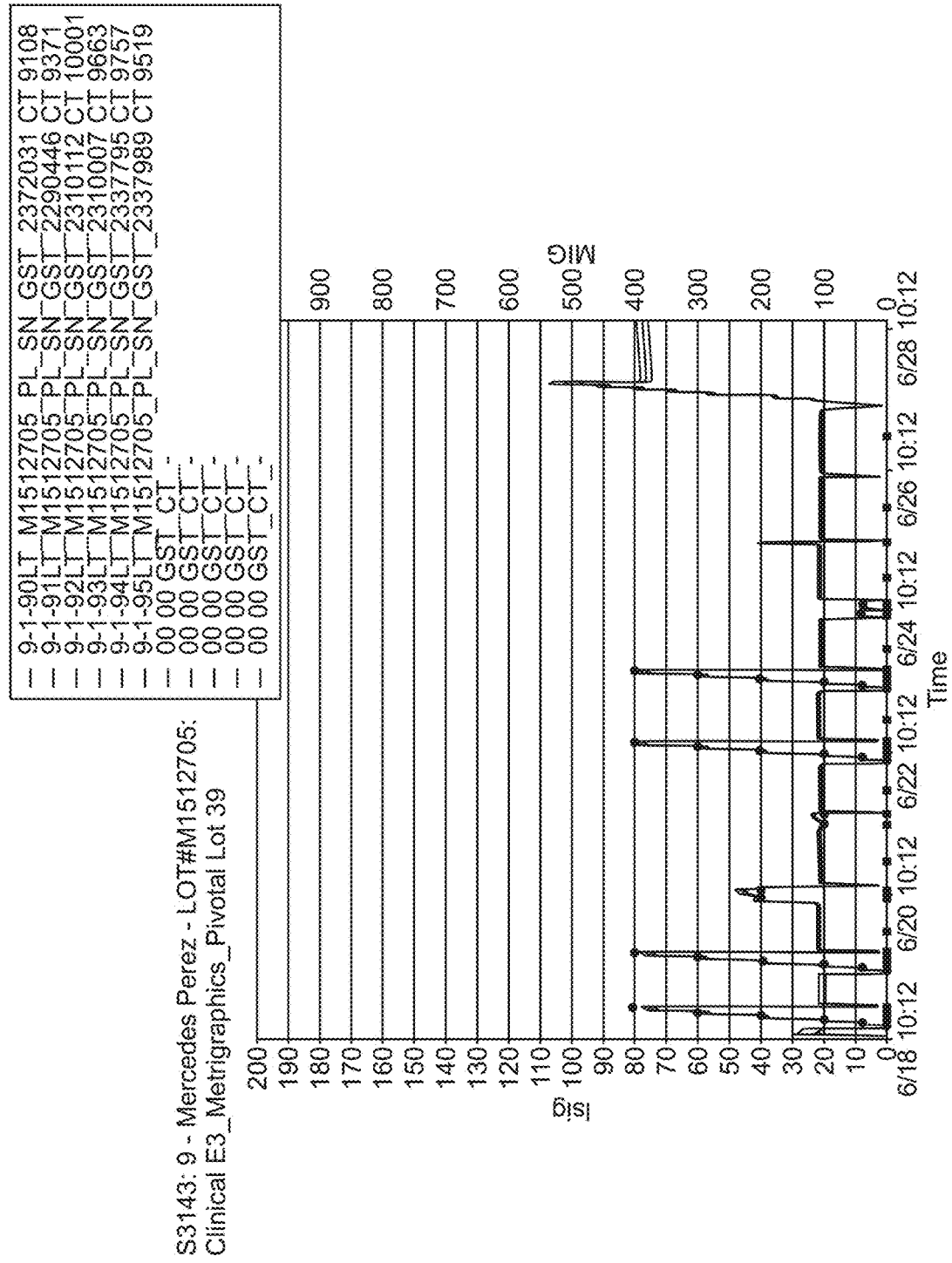
FIG. 5 shows an in vitro SITS data comparison between standard 2×GLM and PCU_GLM (polycarbonate urea glucose limiting membrane), in accordance with one or more embodiments of the invention.
Figure 5:
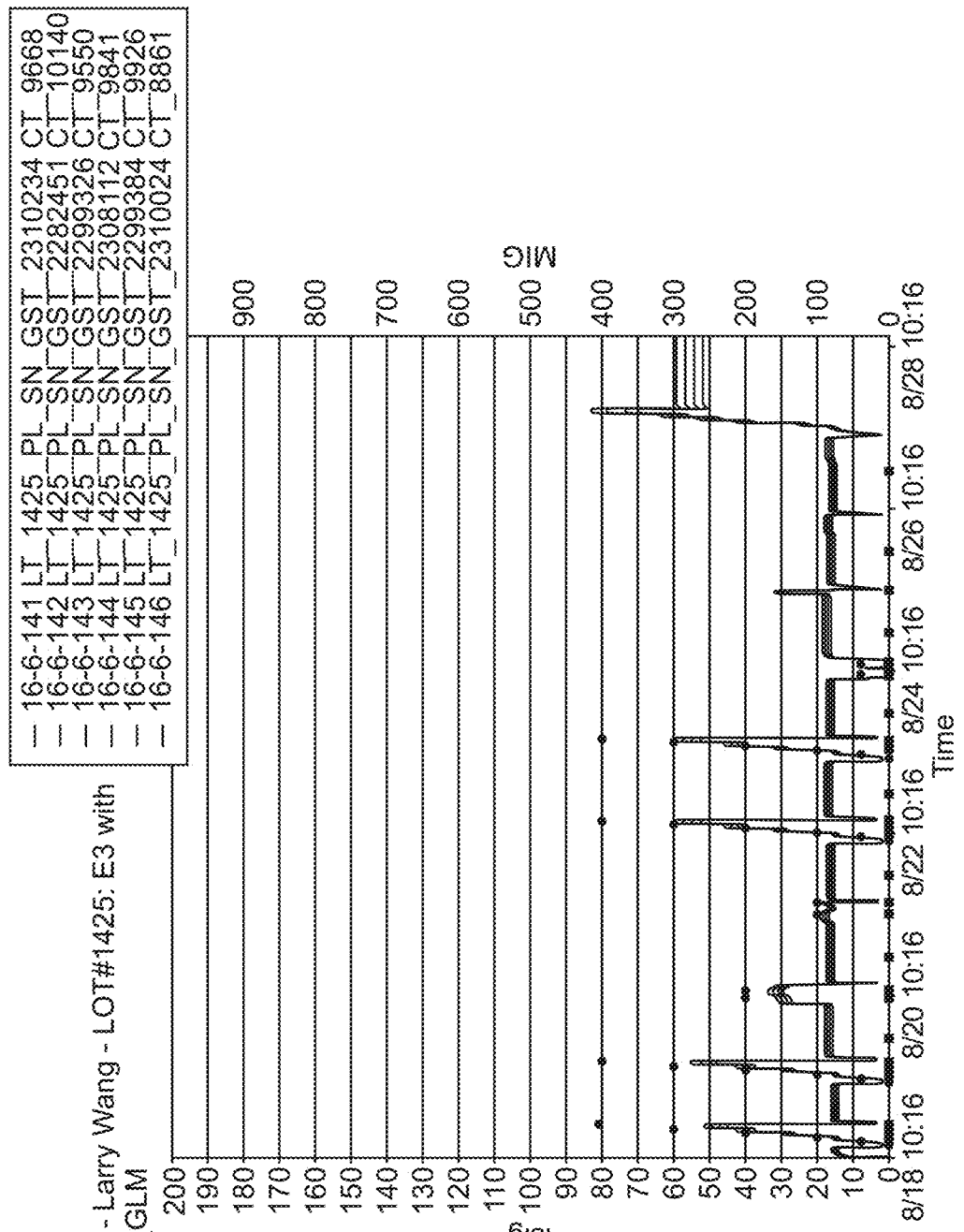
Figure 6:
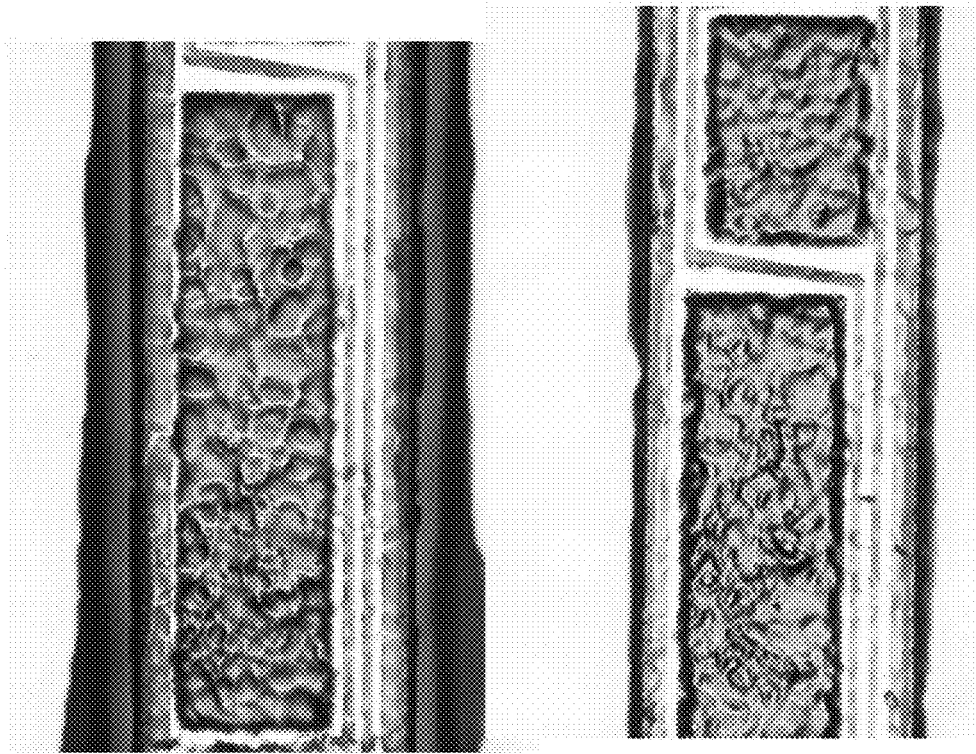
FIG. 6 shows E3 sensor morphology after 7 days SITS testing for standard 2×GLM coated sensors and PCU_GLM coated sensors, in accordance with one or more embodiments of the invention.
Figure 6:
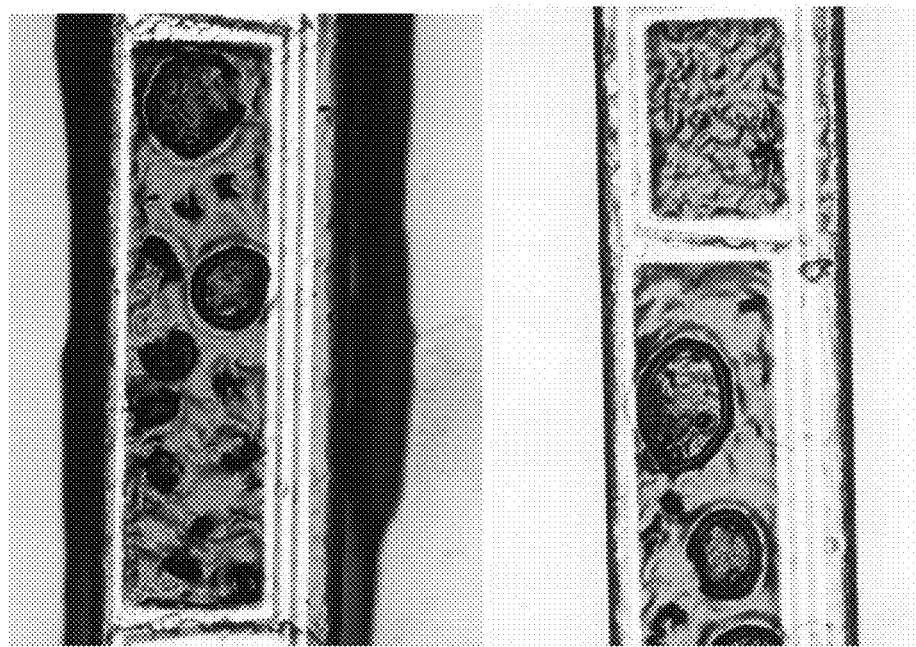
Figure 7C:
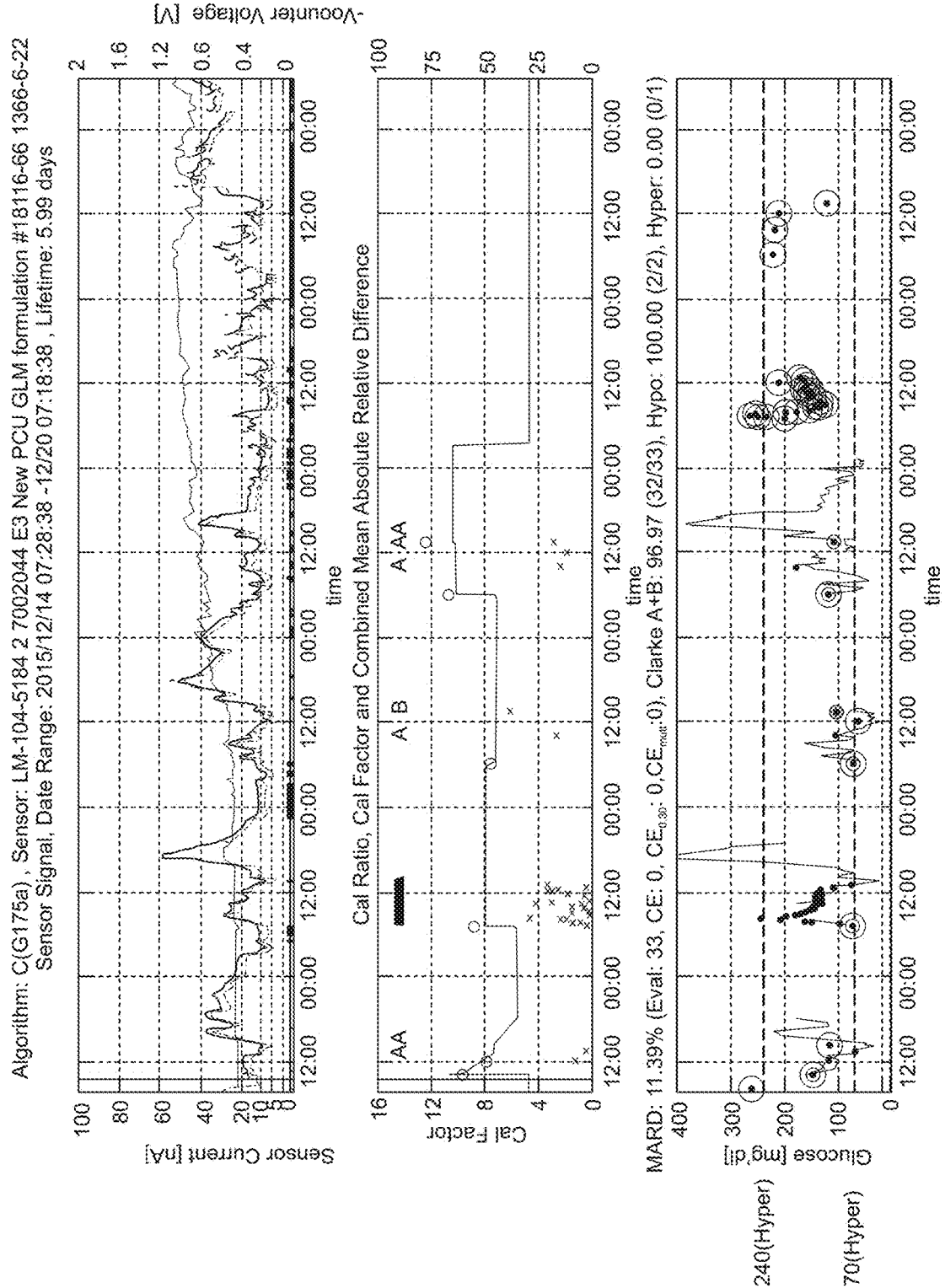
Figure 7D:
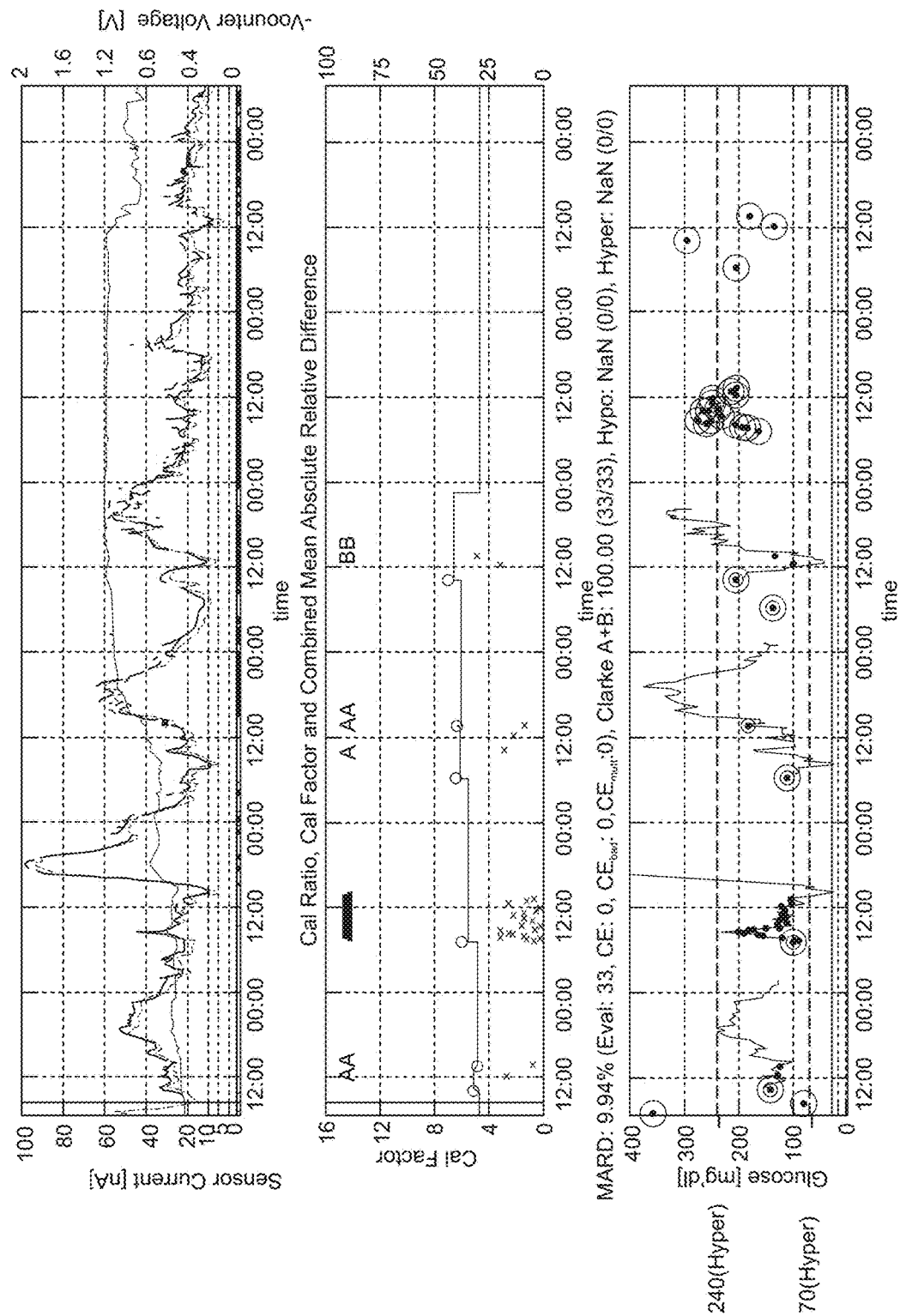
Figure 7E:
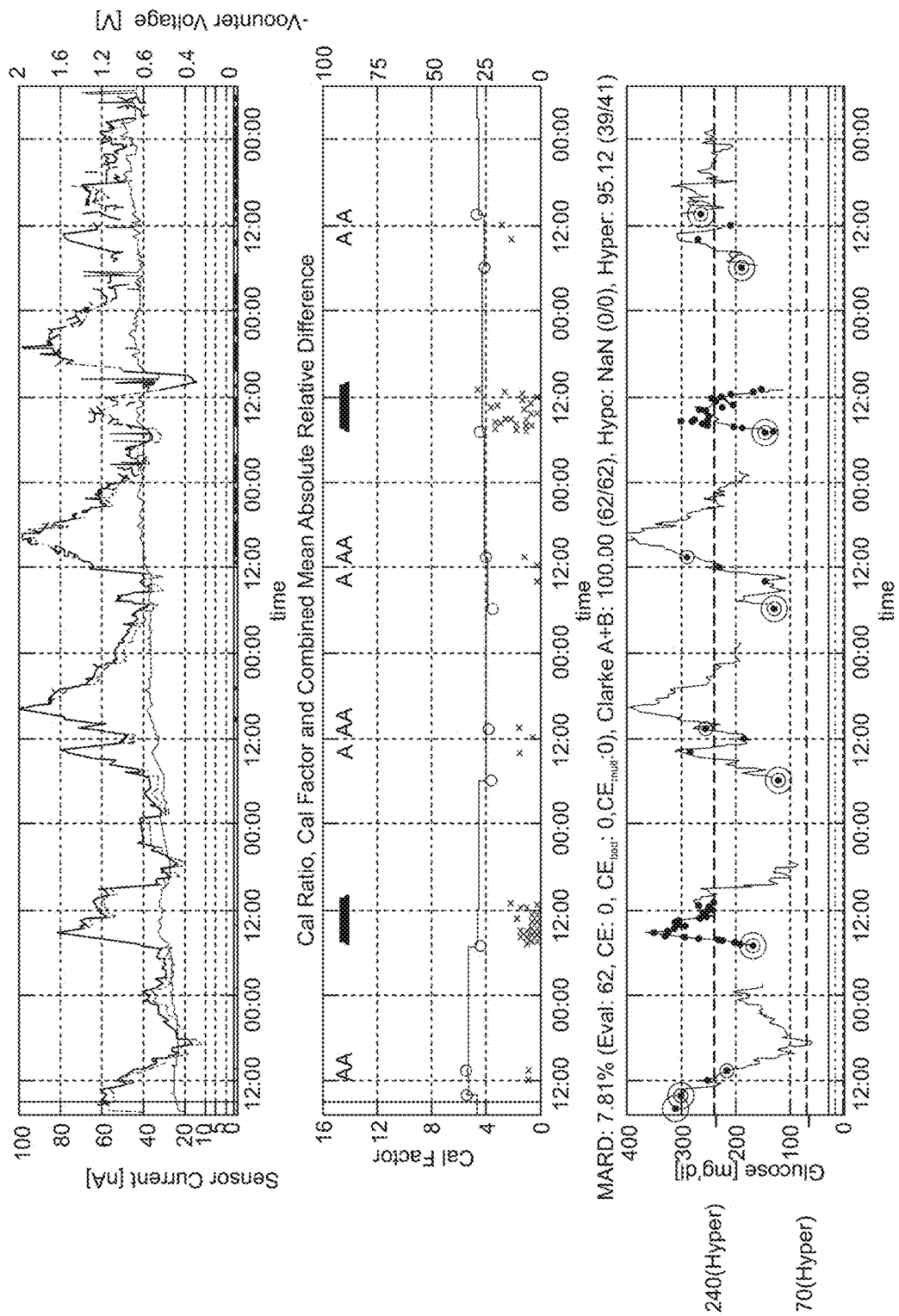

Another reactant used in the preparation of the polyurethane/polyurea polymers described herein is a hydrophilic polymer. The hydrophilic polymer can be a hydrophilic diol, a hydrophilic diamine or a combination thereof. The hydrophilic diol can be a poly(alkylene)glycol, a polyester-based polyol, or a polycarbonate polyol. As used herein, the term "poly(alkylene)glycol" refers to polymers of lower alkylene glycols such as poly(ethylene)glycol, poly(propylene)glycol and polytetramethylene ether glycol (PTMEG). The term "polyester-based polyol" refers to a polymer in which the R group is a lower alkylene group such as ethylene, 1,3-propylene, 1,2-propylene, 1,4-butylene,2,2-dimethyl-1,3-propylene, and the like (e.g. as depicted in FIG. 4 of U.S. Pat. No. 5,777,060). One of skill in the art will also understand that the diester portion of the polymer can also vary from the six-carbon diacid shown. For example, while FIG. 4 of U.S. Pat. No. 5,777,060 illustrates an adipic acid component, the present invention also contemplates the use of succinic acid esters, glutaric acid esters and the like. The term "polycarbonate polyol" refers those polymers having hydroxyl functionality at the chain termini and ether and carbonate functionality within the polymer chain. The alkyl portion of the polymer will typically be composed of C2 to C4 aliphatic radicals, or in some embodiments, longer chain aliphatic radicals, cycloaliphatic radicals or aromatic radicals. The term "hydrophilic diamines" refers to any of the above hydrophilic diols in which the terminal hydroxyl groups have been replaced by reactive amine groups or in which the terminal hydroxyl groups have been derivatized to produce an extended chain having terminal amine groups. For example, a some hydrophilic diamine is a "diamino poly(oxyalkylene)" which is poly(alkylene)glycol in which the terminal hydroxyl groups are replaced with amino groups. The term "diamino poly(oxyalkylene" also refers to poly(alkylene)glycols which have aminoalkyl ether groups at the chain termini. One example of a suitable diamino poly(oxyalkylene) is poly(propylene glycol)bis(2-aminopropyl ether). A number of the above polymers can be obtained from Aldrich Chemical Company. Alternatively, conventional methods known in the art can be employed for their synthesis.

The amount of hydrophilic polymer which is used to make the linear polymer compositions will typically be about 10% to about 80% by mole relative to the diisocyanate which is used. Typically, the amount is from about 20% to about 60% by mole relative to the diisocyanate. When lower amounts of hydrophilic polymer are used, it is common to include a chain extender.

Silicone containing polyurethane/polyurea polymers which are useful in the present invention are typically linear, have excellent oxygen permeability and essentially no glucose permeability. Typically, the silicone polymer is a polydimethylsiloxane having two reactive functional groups (i.e., a functionality of 2). The functional groups can be, for example, hydroxyl groups, amino groups or carboxylic acid groups, but are typically hydroxyl or amino groups. In some embodiments, combinations of silicone polymers can be used in which a first portion comprises hydroxyl groups and a second portion comprises amino groups. Typically, the functional groups are positioned at the chain termini of the silicone polymer. A number of suitable silicone polymers are commercially available from such sources as Dow Chemical Company (Midland, Mich., USA) and General Electric Company (Silicones Division, Schenectady, N.Y., USA). Still others can be prepared by general synthetic methods known in the art (see, e.g. U.S. Pat. No. 5,777,060), beginning with commercially available siloxanes (United Chemical Technologies, Bristol. Pa., USA). For use in the present invention, the silicone polymers will typically be those having a molecular weight of from about 400 to about 10,000, more typically those having a molecular weight of from about 2000 to about 4000. The amount of silicone polymer which is incorporated into the reaction mixture will depend on the desired characteristics of the resulting polymer from which the biocompatible membrane is formed. For those compositions in which a lower glucose penetration is desired, a larger amount of silicone polymer can be employed. Alternatively, for compositions in which a higher glucose penetration is desired, smaller amounts of silicone polymer can be employed. Typically, for a glucose sensor, the amount of siloxane polymer will be from 10% to 90% by mole relative to the diisocyanate. Typically, the amount is from about 20% to 60% by mole relative to the diisocyanate.

In one group of embodiments, the reaction mixture for the preparation of biocompatible membranes will also contain a chain extender which is an aliphatic or aromatic diol, an aliphatic or aromatic diamine, alkanolamine, or combinations thereof (e.g. as depicted in FIG. 8 of U.S. Pat. No. 5,777,060)). Examples of suitable aliphatic chain extenders include ethylene glycol, propylene glycol, 1,4-butanediol, 1,6-hexanediol, ethanolamine, ethylene diamine, butane diamine, 1,4-cyclohexanedimethanol. Aromatic chain extenders include, for example, para-di(2-hydroxyethoxy) benzene, meta-di(2-hydroxyethoxy)benzene, Ethacure 100® (a mixture of two isomers of 2,4-diamino-3,5-diethyltoluene), Ethacure 300® (2,4-diamino-3,5-di(methylthio) toluene), 3,3'-dichloro-4,4'diaminodiphenylmethane, Polacure® 740M (trimethylene glycol bis(para-aminobenzoate) ester), and methylenedianiline. Incorporation of one or more of the above chain extenders typically provides the resulting biocompatible membrane with additional physical strength, but does not substantially increase the glucose permeability of the polymer. Typically, a chain extender is used when lower (i.e., 10-40 mol %) amounts of hydrophilic polymers are used. In particularly some compositions, the chain extender is diethylene glycol which is present in from about 40% to 60% by mole relative to the diisocyanate.

Polymerization of the above reactants can be carried out in bulk or in a solvent system. Use of a catalyst is some, though not required. Suitable catalysts include dibutyltin bis(2-ethylhexanoate), dibutyltin diacetate, triethylamine and combinations thereof. Typically dibutyltin bis(2-ethylhexanoate is used as the catalyst. Bulk polymerization is typically carried out at an initial temperature of about 25° C. (ambient temperature) to about 50° C. (e.g. about 40° C. for THF), in order to insure adequate mixing of the reactants. Upon mixing of the reactants, an exotherm is typically observed, with the temperature rising to about 40-120° C. (e.g. about 40-70° C. for THF). After the initial exotherm, the reaction flask can be heated at from 50° C. to 125° C. (e.g. about 50 to 65° C. for THF), with 50° C. to 100° C. being an exemplary temperature range. Heating is usually carried out for one to two hours. Solution polymerization can be carried out in a similar manner. Solvents which are suitable for solution polymerization include dimethylformamide, dimethyl sulfoxide, dimethylacetamide, halogenated solvents such as 1,2,3-trichloropropane, and ketones such as 4-methyl-2-pentanone. Typically, THF is used as the solvent. When polymerization is carried out in a solvent, heating of the reaction mixture is typically carried out for three to four hours.

Polymers prepared by bulk polymerization are typically dissolved in dimethylformamide and precipitated from water. Polymers prepared in solvents that are not miscible with water can be isolated by vacuum stripping of the solvent. These polymers are then dissolved in dimethylformamide and precipitated from water. After thoroughly washing with water, the polymers can be dried in vacuo at about 50° C. to constant weight.

Preparation of the membranes can be completed by dissolving the dried polymer in a suitable solvent and cast a film onto a glass plate. The selection of a suitable solvent for casting will typically depend on the particular polymer as well as the volatility of the solvent. Typically, the solvent is THF, $CHCl_3$, $CH_2Cl_2$, DMF, IPA or combinations thereof. More typically, the solvent is THF or $DMF/CH_2Cl_2$ (2/98 volume %). The solvent is removed from the films, the resulting membranes are hydrated fully, their thicknesses measured and water pickup is determined. Membranes which are useful in the present invention will typically have a water pickup of about 20 to about 100%, typically 30 to about 90%, and more typically 40 to about 80%, by weight.

Oxygen and glucose diffusion coefficients can also be determined for the individual polymer compositions as well as the polycarbonate polymeric membranes of the present invention. Methods for determining diffusion coefficients are known to those of skill in the art, and examples are provided below. Certain embodiments of the biocompatible membranes described herein will typically have an oxygen diffusion coefficient ($D_{oxygen}$) of about $0.1 \times 10^{-6}$ $cm^2/sec$ to about $2.0 \times 10^{-6}$ $cm^2/sec$ and a glucose diffusion coefficient ($D_{glucose}$) of about $1\times10^{-9}$ cm$^2$/sec to about $500\times10^{-9}$ cm$^2$/sec. More typically, the glucose diffusion coefficient is about $10\times10^{-9}$ cm$^2$/sec to about $200\times10^{-9}$ cm$^2$/sec.

Typical Combinations of Sensor Elements

Embodiments of the invention further include sensors comprising the polycarbonate polymeric compositions disclosed herein in combination with other sensor elements such as an interference rejection membrane (e.g. an interference rejection membrane as disclosed in U.S. patent application Ser. No. 12/572,087, the contents of which are incorporated by reference). One such embodiment of the invention is an interference rejection membrane comprising methacrylate polymers having a molecular weight between 100 and 1000 kilodaltons, wherein the methacrylate polymers are crosslinked by a hydrophilic crosslinking agent such as an organofunctional dipodal alkoxysilane. Another embodiment of the invention is an interference rejection membrane comprising primary amine polymers having a molecular weight between 4,000 Daltons and 500 kilodaltons, wherein the primary amine polymers are crosslinked by a hydrophilic crosslinking agent such as glutaraldehyde. Typically these interference rejection membranes coat a hydrogen peroxide transducing composition. In an illustrative embodiment, the hydrogen peroxide transducing composition comprises an electrode; and the crosslinked interference rejection membrane is coated on the electrode in a layer between 0.1 μm and 1.0 μm thick.

In some embodiments of the invention, an element of the sensor apparatus such as an electrode or an aperture is designed to have a specific configuration and/or is made from a specific material and/or is positioned relative to the other elements so as to facilitate a function of the sensor. In one such embodiment of the invention, a working electrode, a counter electrode and a reference electrode are positionally distributed on the base and/or the conductive layer in a configuration that facilitates sensor start up and/or maintains the hydration of the working electrode, the counter electrode and/or the reference electrode when the sensor apparatus is placed in contact with a fluid comprising the analyte (e.g. by inhibiting shadowing of an electrode, a phenomena which can inhibit hydration and capacitive start-up of a sensor circuit). Typically such embodiments of the invention facilitate sensor start-up and/or initialization.

Optionally embodiments of the apparatus comprise a plurality of working electrodes and/or counter electrodes and/or reference electrodes (e.g. 3 working electrodes, a reference electrode and a counter electrode), in order to, for example, provide redundant sensing capabilities. Certain embodiments of the invention comprising a single sensor. Other embodiments of the invention comprise multiple sensors. In some embodiments of the invention, a pulsed voltage is used to obtain a signal from one or more electrodes of a sensor. Optionally, the plurality of working, counter and reference electrodes are configured together as a unit and positionally distributed on the conductive layer in a repeating pattern of units. In certain embodiments of the invention, the elongated base layer is made from a flexible material that allows the sensor to twist and bend when implanted in vivo; and the electrodes are grouped in a configuration that facilitates an in vivo fluid contacting at least one of working electrode as the sensor apparatus twists and bends when implanted in vivo. In some embodiments, the electrodes are grouped in a configuration that allows the sensor to continue to function if a portion of the sensor having one or more electrodes is dislodged from an in vivo environment and exposed to an ex vivo environment.

In certain embodiments of the invention comprising multiple sensors, elements such as the sensor electrodes are organized/disposed within a flex-circuit assembly. In such embodiments of the invention, the architecture of the sensor system can be designed so that a first sensor does not influence a signal etc. generated by a second sensor (and vice versa); and so that the first and second sensors sense from separate tissue envelopes; so the signals from separate sensors do not interact. At the same time, in typical embodiments of the invention the sensors will be spaced at a distance from each other so that allows them to be easily packaged together and/or adapted to be implanted via a single insertion action. One such embodiment of the invention is an apparatus for monitoring an analyte in a patient, the apparatus comprising: a base element adapted to secure the apparatus to the patient; a first piercing member coupled to and extending from the base element; a first electrochemical sensor operatively coupled to the first piercing member and comprising a first electrochemical sensor electrode for determining at least one physiological characteristic of the patient at a first electrochemical sensor placement site; a second piercing member coupled to and extending from the base element; a second electrochemical sensor operatively coupled to the second piercing member and comprising a second electrochemical sensor electrode for determining at least one physiological characteristic of the patient at a second electrochemical sensor placement site. In such embodiments of the invention, at least one physiological characteristic monitored by the first or the second electrochemical sensor comprises a concentration of a naturally occurring analyte in the patient; the first piercing member disposes the first electrochemical sensor in a first tissue compartment of the patient and the second piercing member disposes the second electrochemical sensor in a second tissue compartment of the patient; and the first and second piercing members are disposed on the base in a configuration selected to avoid a physiological response that can result from implantation of the first electrochemical sensor from altering a sensor signal generated by the second electrochemical sensor.

Various elements of the sensor apparatus can be disposed at a certain location in the apparatus and/or configured in a certain shape and/or be constructed from a specific material so as to facilitate strength and/or function of the sensor. One embodiment of the invention includes an elongated base comprised of a polyimide or dielectric ceramic material that facilitates the strength and durability of the sensor. In certain embodiments of the invention, the structural features and/or relative position of the working and/or counter and/or reference electrodes is designed to influence sensor manufacture, use and/or function. Optionally, the sensor is operatively coupled to a constellation of elements that comprise a flex-circuit (e.g. electrodes, electrical conduits, contact pads and the like). One embodiment of the invention includes electrodes having one or more rounded edges so as to inhibit delamination of a layer disposed on the electrode (e.g. an analyte sensing layer comprising glucose oxidase).

In certain embodiments of the invention, an electrode of the apparatus comprises a platinum composition and the apparatus further comprises a titanium composition disposed between the elongated base layer and the conductive layer. Optionally in such embodiments, apparatus further comprises a gold composition disposed between the titanium composition and the conductive layer. Such embodiments of the invention typically exhibit enhanced bonding between layered materials within the sensor and/or less corrosion and/or improved biocompatibility profiles.

Related embodiments of the invention include methods for inhibiting corrosion of a sensor element and/or method for improving the biocompatibility of a sensor embodiments of the invention (e.g. one constructed to use such materials).

In typical embodiments of the invention, the sensor is operatively coupled to further elements (e.g. electronic components) such as elements designed to transmit and/or receive a signal, monitors, processors and the like as well as devices that can use sensor data to modulate a patient's physiology such as medication infusion pumps. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase and at least one working electrode is not coated with an analyte sensing layer comprising glucose oxidase.

Diagrammatic Illustration of Typical Sensor Configurations

FIG. 1 illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 1. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 1 includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

Figure 2A:
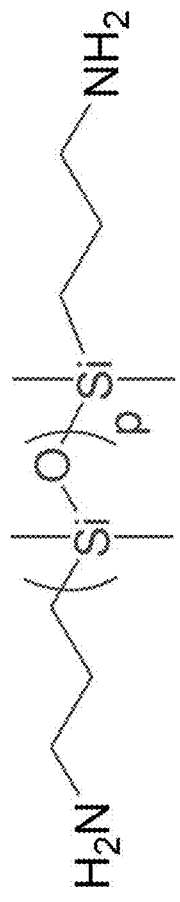
Figure 2A:
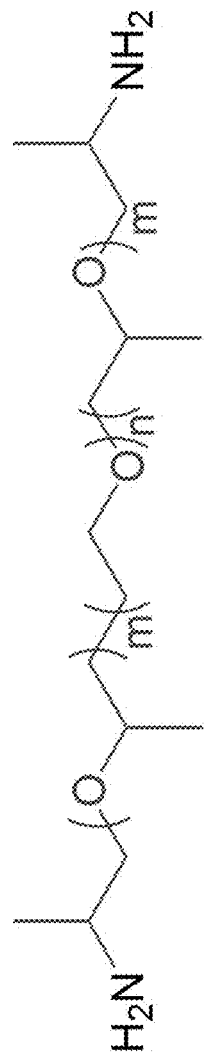
Figure 2B:
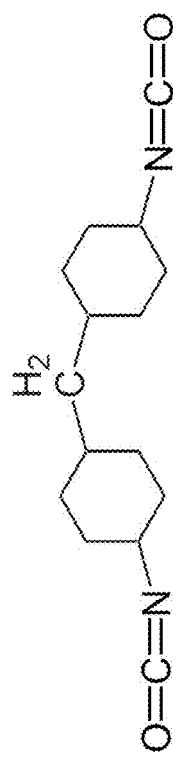
Figure 2B:
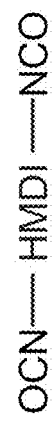
Figure 2B:
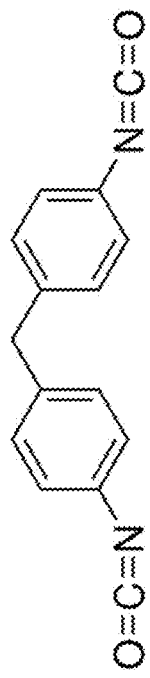
Figure 2B:
Figure 3:
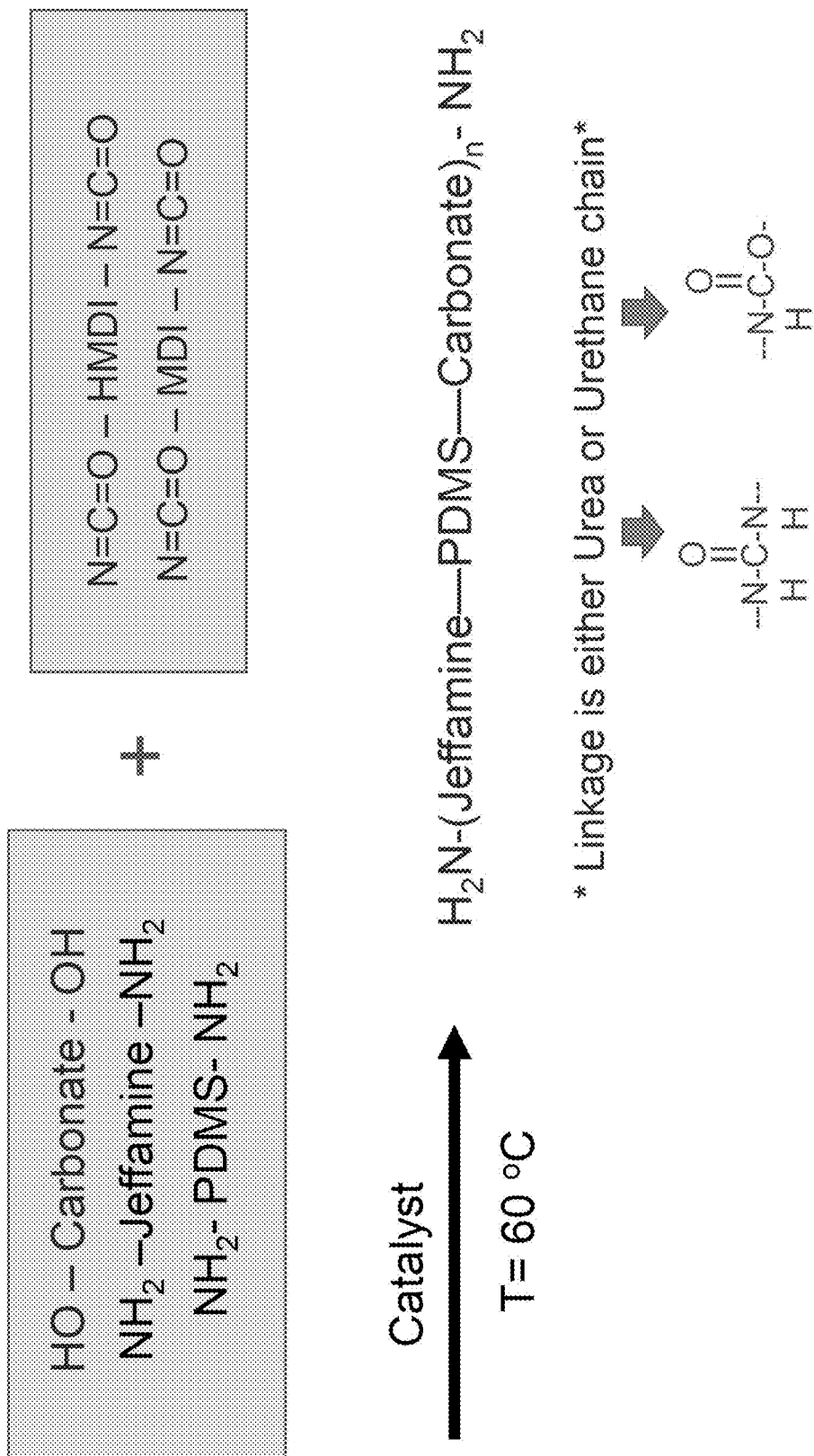
FIG. 3 illustrates a GLM synthesis reaction, in accordance with one or more embodiments of the invention.

In the sensor configuration shown in FIG. 1, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns (μm) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels, the polymer blends disclosed herein or any other suitable hydrophilic membranes known to those skilled in the art.

In some embodiments of the invention, an adhesion promoter layer 114 is disposed between layers such as the analyte modulating layer 112 and the analyte sensing layer 110 as shown in FIG. 1 in order to facilitate their contact and/or adhesion. In a specific embodiment of the invention, an adhesion promoter layer 114 is disposed between the analyte modulating layer 112 and the protein layer 116 as shown in FIG. 1 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g. an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described below.

Base Constituent

Sensors of the invention typically include a base constituent (see, e.g. element 102 in FIG. 1). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 1, the base constituent 102 comprises a ceramic. Alternatively, the base constituent comprises a polymeric material such as a polyimide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 1). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively, the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively, the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention optionally include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size). Examples of interference rejection constituents include one or more layers or coatings of compounds such as hydrophilic crosslinked pHEMA and polylysine polymers as well as cellulose acetate (including cellulose acetate incorporating agents such as poly(ethylene glycol)), polyethersulfones, polytetrafluoroethylenes, the perfluoronated ionomer NAFION, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference. Additional compositions having an unexpected constellation of material properties that make them ideal for use as interference rejection membranes in certain amperometric glucose sensors as well as methods for making and using them are disclosed herein, for example in U.S. patent application Ser. No. 12/572,087.

Analyte Sensing Constituent

The electrochemical sensors of the invention include an analyte sensing constituent disposed on the electrodes of the sensor (see, e.g. element 110 in FIG. 1). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively, the analyte sensing constituent may coat different electrodes to different degrees, with for example the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 1). The term "protein constituent" is used herein according to art accepted terminology and refers to constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 1). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which R' is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase (GOx) to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such a the analyte sensing constituent and/or the protein constituent and or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 1). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$). Typically, the analyte modulating constituent comprises a polycarbonate polymer composition as disclosed herein.

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,439 5,777,060, 5,771,868 and 5,391,250, the disclosures of each being incorporated herein by reference. The hydrogels described therein are particularly useful with a variety of implantable devices for which it is advantageous to provide a surrounding water constituent. In typical embodiments of the invention, the analyte modulating composition includes the polycarbonate polymeric compositions disclosed herein.

Cover Constituent

The electrochemical sensors of the invention include one or more cover constituents which are typically electrically insulating protective constituents (see, e.g. element 106 in FIG. 1). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimagable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

Illustrative Embodiments of Analyte Sensor Apparatus and Associated Characteristics The analyte sensor apparatus disclosed herein has a number of embodiments. A general embodiment of the invention is an analyte sensor apparatus for implantation within a mammal. While the analyte sensors are typically designed to be implantable within the body of a mammal, the sensors are not limited to any particular environment and can instead be used in a wide variety of contexts, for example for the analysis of most liquid samples including biological fluids such as whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

As noted above, the sensor embodiments disclosed herein can be used to sense analytes of interest in one or more physiological environments. In certain embodiments for example, the sensor can be in direct contact with interstitial fluids as typically occurs with subcutaneous sensors. The sensors of the present invention may also be part of a skin surface system where interstitial glucose is extracted through the skin and brought into contact with the sensor (see, e.g. U.S. Pat. Nos. 6,155,992 and 6,706,159 which are incorporated herein by reference). In other embodiments, the sensor can be in contact with blood as typically occurs for example with intravenous sensors. The sensor embodiments of the invention further include those adapted for use in a variety of contexts. In certain embodiments for example, the sensor can be designed for use in mobile contexts, such as those employed by ambulatory users. Alternatively, the sensor can be designed for use in stationary contexts such as those adapted for use in clinical settings. Such sensor embodiments include, for example, those used to monitor one or more analytes present in one or more physiological environments in a hospitalized patient.

Sensors of the invention can also be incorporated in to a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The peroxide sensors of the invention therefore overcome the difficulties observed with such oxygen sensors in non-vascular regions.

Certain peroxide sensor embodiments of the invention further include advantageous long term or "permanent" sensors which are suitable for implantation in a mammal for a time period of greater than 30 days. In particular, as is known in the art (see, e.g. ISO 10993, Biological Evaluation of Medical Devices) medical devices such as the sensors described herein can be categorized into three groups based on implant duration: (1) "Limited" (<24 hours), (2) "Prolonged" (24 hours-30 days), and (3) "Permanent" (>30 days). In some embodiments of the invention, the design of the peroxide sensor of the invention allows for a "Permanent" implantation according to this categorization, i.e. >30 days. In related embodiments of the invention, the highly stable design of the peroxide sensor of the invention allows for an implanted sensor to continue to function in this regard for 2, 3, 4, 5, 6 or 12 or more months.

Permutations of Analyte Sensor Apparatus and Elements

As noted above, the invention disclosed herein includes a number of embodiments including sensors having constellations of elements including polycarbonate polymeric membranes. Such embodiments of the invention allow artisans to generate a variety of permutations of the analyte sensor apparatus disclosed herein. As noted above, illustrative general embodiments of the sensor disclosed herein include a base layer, a cover layer and at least one layer having a sensor element such as an electrode disposed between the base and cover layers. Typically, an exposed portion of one or more sensor elements (e.g., a working electrode, a counter electrode, reference electrode, etc.) is coated with a very thin layer of material having an appropriate electrode chemistry. For example, an enzyme such as lactate oxidase, glucose oxidase, glucose dehydrogenase or hexokinase, can be disposed on the exposed portion of the sensor element within an opening or aperture defined in the cover layer. FIG. 1 illustrates a cross-section of a typical sensor structure 100 of the present invention. The sensor is formed from a plurality of layers of various conductive and non-conductive constituents disposed on each other according to a method of the invention to produce a sensor structure 100.

As noted above, in the sensors of the invention, the various layers (e.g. the analyte sensing layer) of the sensors can have one or more bioactive and/or inert materials incorporated therein. The term "incorporated" as used herein is meant to describe any state or condition by which the material incorporated is held on the outer surface of or within a solid phase or supporting matrix of the layer. Thus, the material "incorporated" may, for example, be immobilized, physically entrapped, attached covalently to functional groups of the matrix layer(s). Furthermore, any process, reagents, additives, or molecular linker agents which promote the "incorporation" of said material may be employed if these additional steps or agents are not detrimental to, but are consistent with the objectives of the present invention. This definition applies, of course, to any of the embodiments of the present invention in which a bioactive molecule (e.g. an enzyme such as glucose oxidase) is "incorporated." For example, certain layers of the sensors disclosed herein include a proteinaceous substance such as albumin which serves as a crosslinkable matrix. As used herein, a proteinaceous substance is meant to encompass substances which are generally derived from proteins whether the actual substance is a native protein, an inactivated protein, a denatured protein, a hydrolyzed species, or a derivatized product thereof. Examples of suitable proteinaceous materials include, but are not limited to enzymes such as glucose oxidase and lactate oxidase and the like, albumins (e.g. human serum albumin, bovine serum albumin etc.), caseins, gamma-globulins, collagens and collagen derived products (e.g., fish gelatin, fish glue, animal gelatin, and animal glue).

An illustrative embodiment of the invention is shown in FIG. 1. This embodiment includes an electrically insulating base layer 102 to support the sensor 100. The electrically insulating layer base 102 can be made of a material such as a ceramic substrate, which may be self-supporting or further supported by another material as is known in the art. In an alternative embodiment, the electrically insulating layer 102 comprises a polyimide substrate, for example a polyimide tape, dispensed from a reel. Providing the layer 102 in this form can facilitate clean, high density mass production. Further, in some production processes using such a polyimide tape, sensors 100 can be produced on both sides of the tape.

Typical embodiments of the invention include an analyte sensing layer disposed on the base layer 102. In an illustrative embodiment as shown in FIG. 1 the analyte sensing layer comprises a conductive layer 104 which is disposed on insulating base layer 102. Typically the conductive layer 104 comprises one or more electrodes. The conductive layer 104 can be applied using many known techniques and materials as will be described hereafter, however, the electrical circuit of the sensor 100 is typically defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating protective cover layer 106 such as a polymer coating is typically disposed on portions of the conductive layer 104. Acceptable polymer coatings for use as the insulating protective layer 106 can include, but are not limited to, non-toxic biocompatible polymers such as polyimide, biocompatible solder masks, epoxy acrylate copolymers, or the like. Further, these coatings can be photo-imagable to facilitate photolithographic forming of apertures 108 through to the conductive layer 104. In certain embodiments of the invention, an analyte sensing layer is disposed upon a porous metallic and/or ceramic and/or polymeric matrix with this combination of elements functioning as an electrode in the sensor.

In the sensors of the present invention, one or more exposed regions or apertures 108 can be made through the protective layer 106 to the conductive layer 104 to define the contact pads and electrodes of the sensor 100. In addition to photolithographic development, the apertures 108 can be formed by a number of techniques, including laser ablation, chemical milling or etching or the like. A secondary photoresist can also be applied to the cover layer 106 to define the regions of the protective layer to be removed to form the apertures 108. An operating sensor 100 typically includes a plurality of electrodes such as a working electrode and a counter electrode electrically isolated from each other, however typically situated in close proximity to one another. Other embodiments may also include a reference electrode. Still other embodiments may utilize a separate reference element not formed on the sensor. The exposed electrodes and/or contact pads can also undergo secondary processing through the apertures 108, such as additional plating processing, to prepare the surfaces and/or strengthen the conductive regions.

An analyte sensing layer 110 is typically disposed on one or more of the exposed electrodes of the conductive layer 104 through the apertures 108. Typically, the analyte sensing layer 110 is a sensor chemistry layer and most typically an enzyme layer. Typically, the analyte sensing layer 110 comprises the enzyme glucose oxidase or the enzyme lactate oxidase. In such embodiments, the analyte sensing layer 110 reacts with glucose to produce hydrogen peroxide which modulates a current to the electrode which can be monitored to measure an amount of glucose present. The sensor chemistry layer 110 can be applied over portions of the conductive layer or over the entire region of the conductive layer. Typically the sensor chemistry layer 110 is disposed on portions of a working electrode and a counter electrode that comprise a conductive layer. Some methods for generating the thin sensor chemistry layer 110 include spin coating processes, dip and dry processes, low shear spraying processes, ink-jet printing processes, silk screen processes and the like. Most typically the thin sensor chemistry layer 110 is applied using a spin coating process.

The analyte sensing layer 110 is typically coated with one or more coating layers. In some embodiments of the invention, one such coating layer includes a membrane which can regulate the amount of analyte that can contact an enzyme of the analyte sensing layer. For example, a coating layer can comprise an analyte modulating membrane layer such as a glucose limiting membrane which regulates the amount of glucose that contacts the glucose oxidase enzyme layer on an electrode. Such glucose limiting membranes can be made from a wide variety of materials known to be suitable for such purposes, e.g., silicone, polyurethane, polyurea cellulose acetate, Nafion, polyester sulfonic acid (Kodak AQ), hydrogels or any other membrane known to those skilled in the art. In certain embodiments of the invention, the analyte modulating layer comprises a linear polyurethane/polyurea polymer polycarbonate with a branched acrylate hydrophilic comb-copolymer having a central chain and a plurality of side chains coupled to the central chain, wherein at least one side chain comprises a silicone moiety.

In some embodiments of the invention, a coating layer is a glucose limiting membrane layer 112 which is disposed above the sensor chemistry layer 110 to regulate glucose contact with the sensor chemistry layer 110. In some embodiments of the invention, an adhesion promoter layer 114 is disposed between the membrane layer 112 and the sensor chemistry layer 110 as shown in FIG. 1 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the sensor chemistry layer 110 can be sufficiently crosslinked or otherwise prepared to allow the membrane layer 112 to be disposed in direct contact with the sensor chemistry layer 110 in the absence of an adhesion promoter layer 114.

As noted above, embodiments of the present invention can include one or more functional coating layers. As used herein, the term "functional coating layer" denotes a layer that coats at least a portion of at least one surface of a sensor, more typically substantially all of a surface of the sensor, and that is capable of interacting with one or more analytes, such as chemical compounds, cells and fragments thereof, etc., in the environment in which the sensor is disposed. Non-limiting examples of functional coating layers include sensor chemistry layers (e.g., enzyme layers), analyte limiting layers, biocompatible layers; layers that increase the slipperiness of the sensor; layers that promote cellular attachment to the sensor; layers that reduce cellular attachment to the sensor; and the like. Typically analyte modulating layers operate to prevent or restrict the diffusion of one or more analytes, such as glucose, through the layers. Optionally such layers can be formed to prevent or restrict the diffusion of one type of molecule through the layer (e.g. glucose), while at the same time allowing or even facilitating the diffusion of other types of molecules through the layer (e.g. $O_2$). An illustrative functional coating layer is a hydrogel such as those disclosed in U.S. Pat. Nos. 5,786,439 and 5,391,250, the disclosures of each being incorporated herein by reference. The hydrogels described therein are particularly useful with a variety of implantable devices for which it is advantageous to provide a surrounding water layer.

The sensor embodiments disclosed herein can include layers having UV-absorbing polymers. In accordance with one aspect of the present invention, there is provided a sensor including at least one functional coating layer including an UV-absorbing polymer. In some embodiments, the UV-absorbing polymer is a polyurethane, a polyurea or a polyurethane/polyurea copolymer. More typically, the selected UV-absorbing polymer is formed from a reaction mixture including a diisocyanate, at least one diol, diamine or mixture thereof, and a polyfunctional UV-absorbing monomer.

UV-absorbing polymers are used with advantage in a variety of sensor fabrication methods, such as those described in U.S. Pat. No. 5,390,671, to Lord et al., entitled "Transcutaneous Sensor Insertion Set"; U.S. Pat. No. 5,165,407, to Wilson et al., entitled "Implantable Glucose Sensor"; and U.S. Pat. No. 4,890,620, to Gough, entitled "Two-Dimensional Diffusion Glucose Substrate Sensing Electrode", which are incorporated herein in their entireties by reference. However, any sensor production method which includes the step of forming an UV-absorbing polymer layer above or below a sensor element is considered to be within the scope of the present invention. In particular, the inventive methods are not limited to thin-film fabrication methods, and can work with other sensor fabrication methods that utilize UV-laser cutting. Embodiments can work with thick-film, planar or cylindrical sensors and the like, and other sensor shapes requiring laser cutting.

As disclosed herein, the sensors of the present invention are particularly designed for use as subcutaneous or transcutaneous glucose sensors for monitoring blood glucose levels in a diabetic patient. Typically each sensor comprises a plurality of sensor elements, for example electrically conductive elements such as elongated thin film conductors, formed between an underlying insulative thin film base layer and an overlying insulative thin film cover layer.

If desired, a plurality of different sensor elements can be included in a single sensor. For example, both conductive and reactive sensor elements can be combined in one sensor, optionally with each sensor element being disposed on a different portion of the base layer. One or more control elements can also be provided. In such embodiments, the sensor can have defined in its cover layer a plurality of openings or apertures. One or more openings can also be defined in the cover layer directly over a portion of the base layer, in order to provide for interaction of the base layer with one or more analytes in the environment in which the sensor is disposed. The base and cover layers can be comprised of a variety of materials, typically polymers. In more specific embodiments the base and cover layers are comprised of an insulative material such as a polyimide. Openings are typically formed in the cover layer to expose distal end electrodes and proximal end contact pads. In a glucose monitoring application, for example, the sensor can be placed transcutaneously so that the distal end electrodes are in contact with patient blood or extracellular fluid, and the contact pads are disposed externally for convenient connection to a monitoring device.

Analyte Sensor Apparatus Configurations

In a clinical setting, accurate and relatively fast determinations of analytes such as glucose and/or lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et al., U.S. Pat. No. 4,536,274, both of which are incorporated herein by reference. As noted below, embodiments of the invention disclosed herein have a wider range of geometrical configurations (e.g. planar) than existing sensors in the art. In addition, certain embodiments of the invention include one or more of the sensors disclosed herein coupled to another apparatus such as a medication infusion pump.

FIG. 2 provides a diagrammatic view of a typical analyte sensor configuration of the current invention. Certain sensor configurations are of a relatively flat "ribbon" type configuration that can be made with the analyte sensor apparatus. Such "ribbon" type configurations illustrate an advantage of the sensors disclosed herein that arises due to the spin coating of sensing enzymes such as glucose oxidase, a manufacturing step that produces extremely thin enzyme coatings that allow for the design and production of highly flexible sensor geometries. Such thin enzyme coated sensors provide further advantages such as allowing for a smaller sensor area while maintaining sensor sensitivity, a highly desirable feature for implantable devices (e.g. smaller devices are easier to implant). Consequently, sensor embodiments of the invention that utilize very thin analyte sensing layers that can be formed by processes such as spin coating can have a wider range of geometrical configurations (e.g. planar) than those sensors that utilize enzyme layers formed via processes such as electrodeposition.

Certain sensor configurations include multiple conductive elements such as multiple working, counter and reference electrodes. Advantages of such configurations include increased surface area which provides for greater sensor sensitivity. For example, one sensor configuration introduces a third working sensor. One obvious advantage of such a configuration is signal averaging of three sensors which increases sensor accuracy. Other advantages include the ability to measure multiple analytes. In particular, analyte sensor configurations that include electrodes in this arrangement (e.g. multiple working, counter and reference electrodes) can be incorporated into multiple analyte sensors. The measurement of multiple analytes such as oxygen, hydrogen peroxide, glucose, lactate, potassium, calcium, and any other physiologically relevant substance/analyte provides a number of advantages, for example the ability of such sensors to provide a linear response as well as ease in calibration and/or recalibration.

An exemplary multiple sensor device comprises a single device having a first sensor which is polarized cathodically and designed to measure the changes in oxygen concentration that occur at the working electrode (a cathode) as a result of glucose interacting with glucose oxidase; and a second sensor which is polarized anodically and designed to measure changes in hydrogen peroxide concentration that occurs at the working electrode (an anode) as a result of glucose coming form the external environment and interacting with glucose oxidase. As is known in the art, in such designs, the first oxygen sensor will typically experience a decrease in current at the working electrode as oxygen contacts the sensor while the second hydrogen peroxide sensor will typically experience an increase in current at the working electrode as the hydrogen peroxide generated as shown in FIG. 1 contacts the sensor. In addition, as is known in the art, an observation of the change in current that occurs at the working electrodes as compared to the reference electrodes in the respective sensor systems correlates to the change in concentration of the oxygen and hydrogen peroxide molecules which can then be correlated to the concentration of the glucose in the external environment (e.g. the body of the mammal).

The analyte sensors of the invention can be coupled with other medical devices such as medication infusion pumps. In an illustrative variation of this scheme, replaceable analyte sensors of the invention can be coupled with other medical devices such as medication infusion pumps, for example by the use of a port couple to the medical device (e.g. a subcutaneous port with a locking electrical connection).

Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al., "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming an analyte sensing layer on the conductive layer, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a linear polyurethane/polyurea polymer polycarbonate with a branched acrylate copolymer having a central chain and a plurality of side chains coupled to the central chain. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, New York (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31.). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electroactive species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photoimagable epoxyacrylate, with an illustrative material comprising a photoimagable polyimide available from OCG, Inc. of West Paterson, N.J., under the product number 7020.

As noted above, appropriate electrode chemistries defining the distal end electrodes can be applied to the sensor tips, optionally subsequent to exposure of the sensor tips through the openings. In an illustrative sensor embodiment having three electrodes for use as a glucose sensor, an enzyme (typically glucose oxidase) is provided within one of the openings, thus coating one of the sensor tips to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor.

Methods for producing the extremely thin enzyme coatings of the invention include spin coating processes, dip and dry processes, low shear spraying processes, ink-jet printing processes, silk screen processes and the like. As artisans can readily determine the thickness of an enzyme coat applied by process of the art, they can readily identify those methods capable of generating the extremely thin coatings of the invention. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes. Consequently, yet another embodiment of the invention is a method of avoiding the electrodeposition influenced cracking and/or delamination of a coating on a sensor comprising applying the coating via a spin coating process.

Methods for Using Analyte Sensor Apparatus of the Invention

A related embodiment of the invention is a method of sensing an analyte within the body of a mammal, the method comprising implanting an analyte sensor embodiment disclosed herein in to the mammal and then sensing an alteration in current at the working electrode and correlating the alteration in current with the presence of the analyte, so that the analyte is sensed. The analyte sensor can polarized anodically such that the working electrode where the alteration in current is sensed is an anode, or cathodically such that the working electrode where the alteration in current is sensed is a cathode. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example, in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and nonvascular spaces.

EXAMPLES

The following examples are given to aid in understanding the invention, but it is to be understood that the invention is not limited to the particular materials or procedures of examples. All materials used in the examples were obtained from commercial sources.

Example 1: Synthesis and Characterization of Illustrative Polyurea/Polyurethane Polymers Using Conventional Methods The disclosure provided herein in combination with what is known in that art confirms that functional linear polyurethane/polyurea polymers can be made from a number of formulations, for example those disclosed in U.S. Pat. Nos. 5,777,060; 5,882,494; 6,642,015; and PCT publications WO 96/30431; WO 96/18115; WO 98/13685; and WO 98/17995, the contents of which are incorporated herein by reference. Certain of these polymers provide formulations useful as a glucose limiting membrane (GLM).

A standard GLM formulation used to make embodiments of the invention comprises:

25 mol % polymethylhydrosiloxane (PDMS), trimethylsilyl terminated, 25-35 centistokes;

75 mol % polypropylene glycol diamine (Jeffamine 600, a polyoxyalkyleneamine with an approximate molecular weight of 600); and 50 mol % of a diisocyanate (e.g., 4,4'-diisocyanate). This standard GLM formulation and processes for its synthesis are disclosed for example in U.S. Pat. Nos. 6,642,015, 5,777,060 and 6,642,015.

Another formulation used in embodiments of the invention is termed a "half permeable GLM", due to the observation that its glucose permeability is one-half of the standard formulation immediately above. In the standard GLM, the Jeffamine/PDMS ration=3/1 (mole ratio). In contrast, in the "half permeable GLM", this ratio is altered so that the Jeffamine/PDMS=12/1. This half-permeable GLM is can be used for example to reduce the weight % of GLM-urea in an overall polymer blend in order to reach a particular Isig (or glucose permeability). Also, the presence of more GLM-acrylate polymer in the polymer blend can enhance the adhesion between polycarbonate polymeric membrane layer and a proximal layer in a sensor (e.g. one comprising glucose oxidase).

The invention claimed is:

1. A method of making an analyte sensor for implantation within a mammal comprising the steps of:
   providing a base layer;
   forming a conductive layer on the base layer, wherein the conductive layer includes a working electrode;
   forming an analyte sensing layer on the conductive layer, wherein the analyte sensing layer includes an oxidoreductase; and
   forming an analyte modulating layer on the analyte sensing layer, wherein:
   the analyte modulating layer comprises a polyurea-urethane copolymer formed from a reaction mixture comprising:
   (a) a diisocyanate;
   (b) a hydrophilic polymer comprising a hydrophilic diol or hydrophilic diamine;
   (c) a siloxane having an amino, hydroxyl or carboxylic acid functional group at a terminus; and
   (d) a polycarbonate diol, wherein:
   the diisocyanate comprises a hexamethylene diisocyanate and/or a methylene diphenyl diisocyanate;
   the hydrophilic polymer comprising a hydrophilic diol or hydrophilic diamine comprises a polyetheramine;
   the siloxane having an amino, hydroxyl or carboxylic acid functional group at a terminus comprises a polydimethylsiloxane; and
   the polycarbonate diol comprises a poly(1,6-hexyl carbonate) diol and/or a poly(1,6 hexyl-1,5 pentyl carbonate) diol; and
   the diisocyanate comprises:
   from 17% to 23% weight percent hexamethylene diisocyanate; and
   from 0% to 8.5% weight percent methylene diphenyl diisocyanate; and
   the polydimethylsiloxane comprises from 14% to 32% weight percent polydimethylsiloxane-A15; and
   the polycarbonate diol comprises from 7.5% to 19% weight percent poly(1,6-hexyl carbonate) diol.

2. The method of claim 1, wherein the polyurea-urethane copolymer is formed from the reaction mixture selected to exhibit an improved thermal stability over time as compared to an equivalent analyte sensor having an analyte modulating layer formed from a comparative reaction mixture that does not include the polycarbonate diol; wherein said improved thermal stability over time comprises a loss of polyurea-urethane copolymer molecular weight after aging at 100% relative humidity (RH) at 60° C. over 6 days that is at least 10% less than the loss of molecular weight after aging at 100% relative humidity (RH) at 60° C. over 6 days that is observed in a polyurea-urethane copolymer formed from a reaction mixture that does not include the polycarbonate diol.

3. The method of claim 1, wherein the polyurea-urethane copolymer is formed from a reaction mixture selected to exhibit an improved resistance to degradation/damage caused by ebeam radiation and/or ethylene oxide as compared to an equivalent analyte sensor having an analyte modulating layer formed from a reaction mixture that does not include the polycarbonate diol.

4. The method of claim 1, wherein the polyurea-urethane copolymer is formed from a reaction mixture selected to exhibit an improved thermal stability over time as compared to an equivalent analyte sensor having an analyte modulating layer formed from a reaction mixture that does not include the polycarbonate diol.

5. The method of claim 1, wherein the polyurea-urethane copolymer is formed from a reaction mixture selected to exhibit an improved resistance to oxidation over time as compared to an equivalent analyte sensor having an analyte modulating layer formed from a reaction mixture that does not include the polycarbonate diol.

6. The method of claim 1, wherein the polyurea-urethane copolymer is formed from a reaction mixture selected to exhibit less deformation over time as compared to an equivalent analyte sensor having an analyte modulating layer formed from a reaction mixture that does not include the polycarbonate diol.

7. The method of claim 1, wherein:
the analyte modulating layer comprises the polyurea-urethane copolymer formed from a reaction mixture comprising:
(a) a diisocyanate present in amounts from 2% to 25% in the polyurea-urethane copolymer formed from the reaction mixture;
(b) a hydrophilic polymer comprising a hydrophilic diol or hydrophilic diamine;
(c) a siloxane having an amino, hydroxyl or carboxylic acid functional group at a terminus; and
(d) a polycarbonate diol, wherein:
the diisocyanate comprises a hexamethylene diisocyanate and/or a methylene diphenyl diisocyanate;
the hydrophilic polymer comprising a hydrophilic diol or hydrophilic diamine comprises a polyetheramine;
the siloxane having an amino, hydroxyl or carboxylic acid functional group at a terminus comprises a polydimethylsiloxane; and
the polycarbonate diol comprises a poly(1,6-hexyl carbonate) diol and/or a poly(1,6 hexyl-1,5 pentyl carbonate) diol.

8. The method of claim 1, wherein the polyurea-urethane copolymer is formed from a reaction mixture selected to exhibit a more uniform glucose permeability profile over time as compared to an equivalent analyte sensor lacking the polyurea-urethane copolymer.

9. The method of claim 1, wherein the analyte sensor is a glucose sensor.

10. The method of claim 1, wherein the conductive layer comprises a plurality of working electrodes and/or counter electrodes and/or reference electrodes; and the plurality of working, counter and reference electrodes are grouped together as a unit and positionally distributed on the conductive layer in a repeating pattern of units.

* * * * *